US006831039B1

United States Patent
Neidlein et al.

(10) Patent No.: US 6,831,039 B1
(45) Date of Patent: Dec. 14, 2004

(54) 3-(HETEROCYCLYL)-SUBSTITUTED BENZOLPYRAZOLS

(75) Inventors: Ulf Neidlein, Mannheim (DE); Norbert Götz, Worms (DE); Ernst Baumann, Dudenhofen (DE); Wolfgang von Deyn, Neustadt (DE); Steffen Kudis, Mannheim (DE); Klaus Langemann, Worms (DE); Guido Mayer, Neustadt (DE); Ulf Misslitz, Neustadt (DE); Matthias Witschel, Ludwigshafen (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/857,067

(22) PCT Filed: Dec. 2, 1999

(86) PCT No.: PCT/EP99/09413

§ 371 (c)(1),
(2), (4) Date: May 31, 2001

(87) PCT Pub. No.: WO00/34273

PCT Pub. Date: Jun. 15, 2000

(30) Foreign Application Priority Data

Aug. 6, 1998 (DE) .......................................... 199 36 514
Dec. 4, 1999 (DE) .......................................... 198 55 850

(51) Int. Cl.⁷ .................... A01N 43/56; A01N 43/80; C07D 261/10; C07D 277/22
(52) U.S. Cl. .................... 504/280; 504/271; 548/364.1; 548/365; 548/364.7; 548/365.1; 548/550; 548/551; 548/214

(58) Field of Search .................. 504/271, 504, 504/280, 282, 221; 548/280, 364.1, 365, 364.7, 365.1, 370.1, 550, 240, 243

(56) References Cited

U.S. PATENT DOCUMENTS

| 4,986,845 A | 1/1991 | Oya et al. ....................... 71/92 |
| 5,175,299 A | 12/1992 | Baba et al. .................. 546/248 |
| 5,545,608 A | 8/1996 | Morimoto et al. .......... 504/282 |
| 5,846,907 A | 12/1998 | von Deyn .................... 504/221 |
| 6,028,034 A | 2/2000 | Geisler et al. .............. 504/246 |
| 6,147,031 A | 11/2000 | Adachi ........................ 504/271 |
| 6,165,944 A | 12/2000 | von Deyn et al. .......... 504/271 |

FOREIGN PATENT DOCUMENTS

| CA | 2278331 | 7/1998 |
| WO | 96/26206 | 8/1996 |
| WO | 98/31681 | 7/1998 |
| WO | 98/31682 | 7/1998 |
| WO | 99/23094 | 5/1999 |

*Primary Examiner*—Sabiha Qazi
(74) *Attorney, Agent, or Firm*—Keil & Weinkauf

(57) ABSTRACT

The invention relates to 3-(heterocyclyl)-substituted benzoylpyrazois of formula (I), wherein the variables have the following meanings: X is O, NH or N-alkyl; $R^1$ is alkyl; $R^2$, $R^3$, $R^4$, $R^5$ are hydrogen, alkyl or alkyl halide; $R^6$ is halogen, nitro, alkyl halide, alkoxy, halogenalkoxy, alkylthio, halogenalkylthio, alkylsulfonyl or halogenalkylsulfonyl; $R^7$ is hydroxy, alkoxy, alkenyloxy, alkylsulfonyloxy, alkylcarboyloxy, alkylthiocarbonyloxy, phenylsulfonyloxy or phenylcarbonyloxy, and the phenyl radical can be substituted; $R^8$, $R^9$ are alkyl; $R^{10}$ is hydrogen or alkyl; and $R^{11}$ is hydrogen or alkyl; and to their agriculturally useable salts. The invention also relates to intermediate products and methods for producing the inventive compounds and to the use of these compounds or products containing them for combating undesirable plants.

13 Claims, No Drawings

3-(HETEROCYCLYL)-SUBSTITUTED BENZOLPYRAZOLS

The present invention relates to 3-(heterocyclyl)-substituted benzoylpyrazoles of the formula I

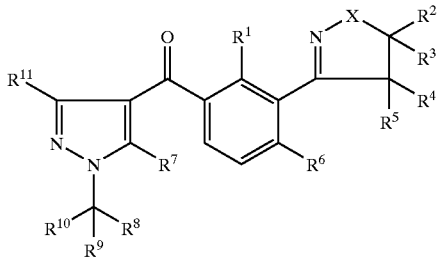

where:
- X is O, NH or N($C_1$–$C_6$-alkyl);
- $R^1$ is $C_1$–$C_6$-alkyl;
- $R^2$, $R^3$, $R^4$, $R^5$ are hydrogen, $C_1$–$C_4$-alkyl or $C_1$–$C_4$-haloalkyl;
- $R^6$ is halogen, nitro, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl or $C_1$–$C_4$-haloalkylsulfonyl;
- $R^7$ is hydroxyl, $C_1$–$C_6$-alkoxy, $C_3$–$C_6$-alkenyloxy, $C_1$–$C_6$-alkylsulfonyloxy, $C_1$–C6-alkylcarbonyloxy, $C_1$–$C_4$-(alkylthio)carbonyloxy, phenylsulfonyloxy or phenylcarbonyloxy, where the phenyl radical of the two last-mentioned substituents may be partially or fully halogenated and/or may carry one to three of the following groups:
  nitro, cyano, $C_1$–$C_4$-alkyl, $C_1$–$C_4$-haloalkyl, $C_1$–$C_4$-alkoxy or $C_1$–$C_4$-haloalkoxy;
- $R^8$, $R^9$ are $C_1$–$C_4$-alkyl;
- $R^{10}$ is hydrogen or $C_1$–$C_4$-alkyl;
  where the number of the carbon atoms of the radicals $R^8$, $R^9$ and $R^{10}$ together is at most 7,
- $R^{11}$ is hydrogen or $C_1$–$C_4$-alkyl;

and their agriculturally useful salts.

Moreover, the invention relates to intermediates and processes for preparing compounds of the formula I, to compositions comprising them and to the use of these derivatives or of compositions comprising them for controlling harmful plants.

Pyrazol-4-yl benzoyl derivatives are disclosed in the literature, for example in WO 96/26206 and WO 98/31681.

However, the herbicidal properties of the prior-art compounds and their compatibility with crop plants are not entirely satisfactory.

It is an object of the present invention to provide novel, in particular herbicidally active, compounds having improved properties.

We have found that this object is achieved by the 3-(heterocyclyl)-substituted benzoylpyrazoles of the formula I and their herbicidal action.

Furthermore, we have found herbicidal compositions which comprise the compounds I and have very good herbicidal action. Moreover, we have found processes for preparing these compositions and methods for controlling undesirable vegetation using the compounds I.

Depending on the substitution pattern, the compounds of the formula I may contain one or more chiral centers, in which case they are present as enantiomers or mixtures of diastereomers. The invention provides both the pure enantiomers or diastereomers and their mixtures.

The compounds of the formula I can also be present in the form of their agriculturally useful salts, the kind of salt usually being immaterial. In general, the salts of those cations or the acid addition salts of those acids are suitable whose cations and anions, respectively, do not adversely affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$–$C_4$-alkyl)sulfonium, and sulfoxonium ions, preferably tri ($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, bicarbonate, carbonate, hexafluorosilicate, hexafluorophosphate, benzoate and the anions of $C_1$–$C_4$-alkanoic acids, preferably formate, acetate, propionate and butyrate.

The organic molecular moieties mentioned for the substituents $R^1$–$R^{11}$ or as radicals on phenyl rings are collective terms for individual enumerations of the individual group members. All hydrocarbon chains, i.e. all alkyl, alkylcarbonyl, haloalkyl, alkoxy, haloalkoxy, alkylcarbonyloxy, (alkylthio)carbonyloxy, alkylsulfonyloxy, alkylthio, haloalkylthio, alkylsulfonyl, haloalkylsulfonyl, alkenyl and alkenyloxy moieties can be straight-chain or branched. Unless indicated otherwise, halogenated substituents preferably carry one to five identical or different halogen atoms. The term "halogen" represents in each case fluorine, chlorine, bromine or iodine.

Examples of other meanings are:

$C_1$–$C_4$-alkyl, and the alkyl moieties of $C_1$–$C_4$-alkylcarbonyl and $C_1$–$C_4$-alkylcarbonyloxy: for example methyl, ethyl, propyl, 1-methylethyl, butyl, 1-methylpropyl, 2-methylpropyl and 1,1-dimethylethyl;

$C_1$–$C_6$-alkyl, and the alkyl moieties of $C_1$–$C_6$-alkylcarbonyl and $C_1$–$C_6$-alkylcarbonyloxy: $C_1$–$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 1-fluoroethyl, 1-chloroethyl, 1-bromoethyl, 1-iodoethyl, 2-fluoroethyl, 2-chloroethyl, 2-bromoethyl, 2-iodethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2- trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-alkoxy: for example methoxy, ethoxy, propoxy, 1-methylethoxy, butoxy, 1-methylpropoxy, 2-methylpropoxy and 1,1-dimethylethoxy;

$C_1$–$C_6$-alkoxy: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylthio, and the alkylthio moieties of $C_1$–$C_4$-(alkylthio)carbonyloxy: for example methylthio, ethylthio, propylthio, 1-methylethylthio, butylthio, 1-methylpropylthio, 2-methylpropylthio and 1,1-dimethylethylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_4$-alkylsulfonyl ($C_1$–$C_4$-alkyl-S(=O)$_2$-), and the alkylsulfonyl moieties of $C_1$–$C_4$-alkylsulfonyloxy: for example methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl, and the alkylsulfonyl moieties of $C_1$–C6-alkylsulfonyloxy: a $C_1$–$C_4$-alkylsulfonyl radical as mentioned above, and also, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_4$-haloalkylsulfonyl: a $C_1$–$C_4$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl and nonafluorobutylsulfonyl;

$C_3$–$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, Hex-5- en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-3-en-1-yloxy, 1,2-dimethylbut-2-en-1-yloxy, 1,2-dimethylbut-3-en-1-yloxy, 1,3-dimethylbut-3-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-3-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-3-en-1-yloxy, 1-ethylbut-2-en-1-yloxy, 1-ethylbut-3-en-1-yloxy, 2-ethylbut-3-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy and 1-ethyl-2-methylprop-2-en-1-yloxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl1-1-methylprop-2-en-1-yl, 1-ethyl-2-methylprop-1-en-1-yl and 1-ethyl-2-methylprop-2-en-1-yl.

The phenyl rings are preferably unsubstituted or carry one to three halogen atoms and/or one nitro group, one cyano group, one or two methyl, trifluoromethyl, methoxy or trifluoromethoxy groups.

Emphasis is given to those 3-(heterocyclyl)-substituted benzoylpyrazoles of the formula I where $R^7$ is hydroxyl, $C_1$–$C_6$-alkoxy, $C_3$–$C_6$-alkenyloxy, $C_1$–$C_6$-alkyl-sulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

Preference is given to the 3-(heterocyclyl)-substituted benzoylpyrazoles of the formula I where:

X is O;

$R^1$ is $C_1$–$C_4$-alkyl;
particularly preferably methyl or ethyl;
with particular preference methyl;

$R^2$, $R^3$, $R^4$, $R^5$ are hydrogen, $C_1$–$C_4$-alkyl or $C_1$–$C_4$-haloalkyl;
particularly preferably hydrogen, methyl, ethyl, propyl, 1-methylethyl, fluoromethyl or chloromethyl;
with particular preference hydrogen, methyl, ethyl or chloromethyl;

$R^6$ is $C_1$–$C_4$-alkylthio or $C_1$–$C_4$-alkylsulfonyl;
particularly preferably methylthio, ethylthio or 1-methyl-1-ethylthio, methylsulfonyl, ethylsulfonyl, 1-methylethylsulfonyl or propylsulfonyl;
with particular preference methylsulfonyl, ethylsulfonyl, 1-methylethylsulfonyl or propylsulfonyl;

$R^7$ is hydroxyl, $C_1$–$C_6$-alkoxy, $C_3$–$C_6$-alkenyloxy, $C_1$–$C_6$-alkylsulfonyloxy, $C_1$–$C6$-alkylcarbonyloxy, $C_1$–$C_4$-(alkylthio)carbonyloxy, phenylsulfonyloxy or phenylcarbonyloxy, where the phenyl radical of the two last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy;
particularly preferably hydroxyl, $C_1$–$C_4$-alkoxy, $C_3$–$C_6$-alkenyloxy, $C_1$–$C_4$-alkylsulfonyloxy, $C_1$–$C_4$-alkylcarbonyloxy, phenylsulfonyloxy or phenylcarbonyloxy, where the phenyl radical of the two last-mentioned substituents may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy;

$R^8$, $R^9$ are $C_1$–$C_4$-alkyl;
particularly preferably methyl, ethyl, propyl, 1-methyl-1-ethyl, butyl, 1-methyl-1-propyl and 2-methyl-1-propyl;

$R^{10}$ is hydrogen or $C_1$–C4-alkyl;
particularly preferably $C_1$–$C_4$-alkyl;
with particular preference methyl, ethyl or propyl;

$R^{11}$ is hydrogen or $C_1$–$C_4$-alkyl;
particularly preferably hydrogen or methyl.

Particular preference is given to the 3-(heterocyclyl)-substituted benzoylpyrazoles of the formula I where X is O;

$R^1$ is $C_1$–$C_4$-alkyl;
particularly preferably methyl or ethyl;
with particular preference methyl;

$R^6$ is $C_1$–$C_4$-alkylsulfonyl; particularly preferably methylsulfonyl, ethylsulfonyl, 1-methyl-1-ethylsulfonyl or propylsulfonyl;

$R^7$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^8$, $R^9$ are $C_1$–$C_4$-alkyl;

$R^{10}$ is hydrogen or $C_1$–C4-alkyl.

Very particular preference is given to the 3-(heterocyclyl)-substituted benzoylpyrazoles of the formula I where $R^8$ is $C_2$–$C_4$-alkyl, for example ethyl, 1-methyl-1-ethyl, propyl or butyl;

$R^9$ is $C_1$–$C_4$-alkyl, for example methyl or ethyl;

$R^{10}$ is hydrogen or $C_1$–$C_4$-alkyl, for example methyl or ethyl.

Very particular preference is also given to the 3-(heterocyclyl)-substituted benzoylpyrazoles of the formula I where $R^8$ is methyl;

$R^9$ is $C_1$–$C_4$-alkyl, for example methyl, ethyl, propyl or butyl;

$R^{10}$ is $C_1$–$C_4$-alkyl, for example methyl or ethyl.

Very particular preference is also given to the 3-(heterocyclyl)-substituted benzoylpyrazoles of the formula I where $R^8$, $R^9$ are methyl;

$R^{10}$ is hydrogen.

Preference is also given to the 3-(heterocyclyl)-substituted benzoylpyrazoles of the formula I where:

X is O $R^1$ is $C_1$–$C_4$-alkyl; particularly preferably methyl or ethyl; with particular preference methyl;

$R^2$, $R^3$, $R^4$, $R^5$ are hydrogen, $C_1$–$C_4$-alkyl or $C_1$–$C_4$-haloalkyl; particularly preferably hydrogen, methyl, ethyl, propyl, 1-methyl-1-ethyl, chloromethyl or fluoromethyl;

with particular preference hydrogen, methyl, ethyl or chloromethyl;

$R^6$ is halogen, nitro, $C_1$–$C_4$-haloalkyl, $C_1$–$C_4$-alkoxy or $C_1$–$C_4$-haloalkoxy;

particularly preferably halogen, such as chlorine or bromine, nitro, $C_1$–$C_2$-haloalkyl, such as difluoromethyl or trifluoromethyl, $C_1$–$C_2$-alkoxy or $C_1$–$C_2$-haloalkoxy, such as difluoromethoxy, chlorodifluoromethoxy or trifluoromethoxy;

$R^7$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, $C_1$–$C_4$-(alkylthio)carbonyloxy, phenylsulfonyloxy or phenylcarbonyloxy, where the phenyl radical of the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

particularly preferably hydroxyl, $C_1$–$C_4$-alkoxy, $C_3$–$C_6$-alkenyloxy, $C_1$–$C_4$-alkylsulfonyloxy, $C_1$–$C_4$-alkylcarbonyloxy, phenylsulfonyloxy or phenylcarbonyloxy, where the phenyl radical of the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

$R^8$, $R^9$ are $C_1$–$C_4$-alkyl; particularly preferably methyl, ethyl, propyl, 1-methyl-1-ethyl, butyl, 1-methyl-1-propyl and 2-methyl-1-propyl;

$R^{10}$ is hydrogen or $C_1$–$C_4$-alkyl; particularly preferably $C_1$–$C_4$-alkyl; with particular preference methyl, ethyl or propyl;

$R^{11}$ is hydrogen or $C_1$–$C_4$-alkyl; particularly preferably hydrogen or methyl.

Particular preference is given to the 3-(heterocyclyl)-substituted benzoylpyrazoles of the formula I where X is O $R^1$ is $C_1$–$C_4$-alkyl; particularly preferably methyl or ethyl; with particular preference methyl;

$R^6$ is halogen, nitro, $C_1$–$C_4$-haloalkyl, $C_1$–$C_4$-alkoxy or $C_1$–$C_4$-haloalkoxy;

particularly preferably halogen, such as chlorine a or bromine, nitro, $C_1$–$C_2$-haloalkyl, such as difluoromethyl or trifluoromethyl, $C_1$–$C_2$-alkoxy or $C_1$–$C_2$-haloalkoxy, such as difluoromethoxy;

$R^7$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl;

$R^8$, $R^9$ are $C_1$–$C_4$-alkyl;

$R^{10}$ is hydrogen or $C_1$–$C_4$-alkyl.

very particular preference is given to the 3-(heterocyclyl)-substituted benzoylpyrazoles of the formula I where $R^8$ is $C_2$–$C_4$-alkyl, for example ethyl, 1-methyl-1-ethyl, propyl or butyl;

$R^9$ is $C_1$–$C_4$-alkyl, for example methyl or ethyl;

$R^{10}$ is hydrogen or $C_1$–$C_4$-alkyl, for example methyl or ethyl.

Very particular preference is also given to the 3-(heterocyclyl)-substituted benzoylpyrazoles of the formula I where $R^8$ is methyl;

$R^9$ is $C_1$–$C_4$-alkyl, for example methyl, ethyl, propyl or butyl;

$R^{10}$ is $C_1$–$C_4$-alkyl, for example methyl or ethyl.

Very particular preference is also given to the 3-(heterocyclyl)-substituted benzoylpyrazoles of the formula I where $R^8$, $R^9$ are methyl;

$R^{10}$ is hydrogen.

Preference is also given to the 3-(heterocyclyl)-substituted benzoylpyrazoles of the formula I where:

X is $N(C_1$–$C_6$-alkyl);

particularly preferably N-methyl, N-ethyl, N-(1-methyl-1-ethyl) or N-propyl;

$R^1$ is $C_1$-C6-alkyl;

particularly preferably methyl or ethyl;

with particular preference methyl;

$R^2$, $R^3$, $R^4$, $R^5$ are hydrogen, $C_1$–$C_4$-alkyl or $C_1$–$C_4$-haloalkyl;

particularly preferably hydrogen, methyl, ethyl, propyl, 1-methyl-1-ethyl, fluoromethyl or chloromethyl; with particular preference hydrogen, methyl, ethyl or chloromethyl;

$R^6$ is halogen, nitro, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl or $C_1$–$C_4$-haloalkylsulfonyl;

particularly preferably halogen, such as fluorine, chlorine or bromine, nitro, $C_1$–$C_4$-haloalkyl, such as difluoromethyl or trifluoromethyl, $C_1$–$C_4$-alkoxy, such as methoxy or ethoxy, $C_1$–$C_4$-haloalkoxy, such as difluoromethoxy, chlorodifluoromethoxy or trifluoromethoxy, $C_1$–$C_4$-alkylthio, such as methylthio or ethylthio, or $C_1$–$C_4$-alkylsulfonyl, such as methylsulfonyl, ethylsulfonyl, 1-methyl-1-ethylsulfonyl or propylsulfonyl;

$R^7$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, $C_1$–$C_4$-(alkylthio)carbonyloxy, phenylsulfonyloxy or phenylcarbonyloxy, where the phenyl radical of the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy; particularly preferably hydroxyl, $C_1$–$C_4$-alkoxy, $C_3$–$C_6$-alkenyloxy, $C_1$–$C_4$-alkylsulfonyloxy, $C_1$–$C_4$-alkylcarbonyloxy, phenylsulfonyloxy or phenylcarbonyloxy, where the phenyl radical of the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

$R^8$, $R^9$ are $C_1$–$C_4$-alkyl;

particularly preferably methyl, ethyl, propyl, 1-methyl-1-ethyl, butyl, 1-methyl-1-propyl and 2-methyl-1-propyl;

$R^{10}$ is hydrogen or $C_1$–$C_4$-alkyl;

particularly preferably $C_1$–$C_4$-alkyl;

with particular preference methyl, ethyl or propyl;

$R^{11}$ is hydrogen or $C_1$–$C_4$-alkyl; particularly preferably hydrogen or methyl.

Particular preference is given to the 3-heterocyclyl-substituted benzoylpyrazoles of the formula I where $R^7$ is hydroxyl, $C_1$–$C_6$-alkylsulfonyloxy, $C_1$–$C_6$-alkylcarbonyloxy, phenylsulfonyloxy or phenylcarbonyloxy, where the phenyl radical of the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$-C4-haloalkoxy;

particularly preferably hydroxyl.

Preference is likewise given to the 3-(heterocyclyl)-substituted benzoylpyrazoles of the formula I in which the variables are as defined below:

X is O;

$R^1$ is $C_1$–$C_4$-alkyl;

particularly preferably methyl or ethyl;

$R^2$, $R^3$, $R^4$, $R^5$ are hydrogen, $C_1$–$C_4$-alkyl or $C_1$–$C_4$-haloalkyl;

particularly preferably hydrogen or $C_1$–$C_4$-haloalkyl;

$R^6$ is $C_1$–$C_4$-alkylsulfonyl;

particularly preferably methylsulfonyl;

$R^7$ is hydroxyl, $C_1$–$C_6$-alkoxy, $C_1$–$C_6$-alkylcarbonyloxy, $C_1$–C4-(alkylthio)carbonyloxy, phenylsulfonyloxy or phenylcarbonyloxy, where the phenyl radical of the two last-mentioned substituents may be partially or fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy;

particularly preferably hydroxyl, $C_1$–$C_4$-alkoxy or phenylcarbonyloxy, where the phenyl radical may be [lacuna] or fully halogenated and/or may carry one to three $C_1$–$C_4$-haloalkyl radicals;

$R^8$, $R^9$ are $C_1$–$C_4$-alkyl;

$R^{10}$ is hydrogen or $C_1$–$C_4$-alkyl;

$R^{11}$ is hydrogen or $C_1$–$C_4$-alkyl.

Very particular preference is given to the compounds of the formula Ia1 (≡I where $R^1$, $R^8$, $R^9$ =$CH_3$; $R^{10}$, $R^{11}$=H), in particular to the compounds Ia1.1 to Ia1.300 of Table 1, where the radical definitions X and $R^1$ to $R^{11}$ are of particular importance for the compounds according to the invention, not only in combination with one another, but in each case also on their own.

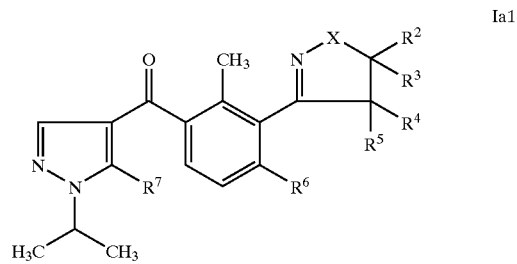

Ia1

TABLE 1

| No. | X | $R^2$ | $R^3$ | $R^4$ | $R^5$ | $R^6$ | $R^7$ |
|---|---|---|---|---|---|---|---|
| Ia1.1 | O | H | H | H | H | $SCH_3$ | OH |
| Ia1.2 | O | H | H | H | H | $SCH_2CH_3$ | OH |
| Ia1.3 | O | H | H | H | H | $SO_2CH_3$ | OH |
| Ia1.4 | O | H | H | H | H | $SO_2CH_2CH_3$ | OH |
| Ia1.5 | O | H | H | H | H | $SO_2CH(CH_3)_2$ | OH |
| Ia1.6 | O | H | H | H | H | $SO_2(CH_2)_2CH_3$ | OH |
| Ia1.7 | O | H | H | H | H | Cl | OH |
| Ia1.8 | O | H | H | H | H | Br | OH |
| Ia1.9 | O | H | H | H | H | $NO_2$ | OH |
| Ia1.10 | O | H | H | H | H | $CHF_2$ | OH |
| Ia1.11 | O | H | H | H | H | $CF_3$ | OH |
| Ia1.12 | O | H | H | H | H | $OCH_3$ | OH |
| Ia1.13 | O | H | H | H | H | $OCH_2CH_3$ | OH |
| Ia1.14 | O | H | H | H | H | $OCHF_2$ | OH |
| Ia1.15 | O | H | H | H | H | $OCF_3$ | OH |
| Ia1.16 | O | $CH_3$ | H | H | H | $SCH_3$ | OH |
| Ia1.17 | O | $CH_3$ | H | H | H | $SCH_2CH_3$ | OH |
| Ia1.18 | O | $CH_3$ | H | H | H | $SO_2CH_3$ | OH |
| Ia1.19 | O | $CH_3$ | H | H | H | $SO_2CH_2CH_3$ | OH |
| Ia1.20 | O | $CH_3$ | H | H | H | $SO_2CH(CH_3)_2$ | OH |
| Ia1.21 | O | $CH_3$ | H | H | H | $SO_2(CH_2)_2CH_3$ | OH |
| Ia1.22 | O | $CH_3$ | H | H | H | Cl | OH |
| Ia1.23 | O | $CH_3$ | H | H | H | Br | OH |
| Ia1.24 | O | $CH_3$ | H | H | H | $NO_2$ | OH |
| Ia1.25 | O | $CH_3$ | H | H | H | $CHF_2$ | OH |
| Ia1.26 | O | $CH_3$ | H | H | H | $CF_3$ | OH |
| Ia1.27 | O | $CH_3$ | H | H | H | $OCH_3$ | OH |
| Ia1.28 | O | $CH_3$ | H | H | H | $OCH_2CH_3$ | OH |
| Ia1.29 | O | $CH_3$ | H | H | H | $OCHF_2$ | OH |
| Ia1.30 | O | $CH_3$ | H | H | H | $OCF_3$ | OH |
| Ia1.31 | O | H | H | $CH_3$ | H | $SCH_3$ | OH |
| Ia1.32 | O | H | H | $CH_3$ | H | $SCH_2CH_3$ | OH |
| Ia1.33 | O | H | H | $CH_3$ | H | $SO_2CH_3$ | OH |
| Ia1.34 | O | H | H | $CH_3$ | H | $SO_2CH_2CH_3$ | OH |
| Ia1.35 | O | H | H | $CH_3$ | H | $SO_2CH(CH_3)_2$ | OH |
| Ia1.36 | O | H | H | $CH_3$ | H | $SO_2(CH_2)_2CH_3$ | OH |
| Ia1.37 | O | H | H | $CH_3$ | H | Cl | OH |
| Ia1.38 | O | H | H | $CH_3$ | H | Br | OH |
| Ia1.39 | O | H | H | $CH_3$ | H | $NO_2$ | OH |
| Ia1.40 | O | H | H | $CH_3$ | H | $CHF_2$ | OH |

TABLE 1-continued

| No. | X | R² | R³ | R⁴ | R⁵ | R⁶ | R⁷ |
|---|---|---|---|---|---|---|---|
| Ia1.41 | O | H | H | CH₃ | H | CF₃ | OH |
| Ia1.42 | O | H | H | CH₃ | H | OCH₃ | OH |
| Ia1.43 | O | H | H | CH₃ | H | OCH₂CH₃ | OH |
| Ia1.44 | O | H | H | CH₃ | H | OCHF₂ | OH |
| Ia1.45 | O | H | H | CH₃ | H | OCF₃ | OH |
| Ia1.46 | O | CH₃ | CH₃ | H | H | SCH₃ | OH |
| Ia1.47 | O | CH₃ | CH₃ | H | H | SCH₂CH₃ | OH |
| Ia1.48 | O | CH₃ | CH₃ | H | H | SO₂CH₃ | OH |
| Ia1.49 | O | CH₃ | CH₃ | H | H | SO₂CH₂CH₃ | OH |
| Ia1.50 | O | CH₃ | CH₃ | H | H | SO₂CH(CH₃)₂ | OH |
| Ia1.51 | O | CH₃ | CH₃ | H | H | SO₂(CH₂)₂CH₃ | OH |
| Ia1.52 | O | CH₃ | CH₃ | H | H | Cl | OH |
| Ia1.53 | O | CH₃ | CH₃ | H | H | Br | OH |
| Ia1.54 | O | CH₃ | CH₃ | H | H | NO₂ | OH |
| Ia1.55 | O | CH₃ | CH₃ | H | H | CHF₂ | OH |
| Ia1.56 | O | CH₃ | CH₃ | H | H | CF₃ | OH |
| Ia1.57 | O | CH₃ | CH₃ | H | H | OCH₃ | OH |
| Ia1.58 | O | CH₃ | CH₃ | H | H | OCH₂CH₃ | OH |
| Ia1.59 | O | CH₃ | CH₃ | H | H | OCHF₂ | OH |
| Ia1.60 | O | CH₃ | CH₃ | H | H | OCF₃ | OH |
| Ia1.61 | O | CH₃ | H | CH₃ | H | SCH₃ | OH |
| Ia1.62 | O | CH₃ | H | CH₃ | H | SCH₂CH₃ | OH |
| Ia1.63 | O | CH₃ | H | CH₃ | H | SO₂CH₃ | OH |
| Ia1.64 | O | CH₃ | H | CH₃ | H | SO₂CH₂CH₃ | OH |
| Ia1.65 | O | CH₃ | H | CH₃ | H | SO₂CH(CH₃)₂ | OH |
| Ia1.66 | O | CH₃ | H | CH₃ | H | SO₂(CH₂)₂CH₃ | OH |
| Ia1.67 | O | CH₃ | H | CH₃ | H | Cl | OH |
| Ia1.68 | O | CH₃ | H | CH₃ | H | Br | OH |
| Ia1.69 | O | CH₃ | H | CH₃ | H | NO₂ | OH |
| Ia1.70 | O | CH₃ | H | CH₃ | H | CHF₂ | OH |
| Ia1.71 | O | CH₃ | H | CH₃ | H | CF₃ | OH |
| Ia1.72 | O | CH₃ | H | CH₃ | H | OCH₃ | OH |
| Ia1.73 | O | CH₃ | H | CH₃ | H | OCH₂CH₃ | OH |
| Ia1.74 | O | CH₃ | H | CH₃ | H | OCHF₂ | OH |
| Ia1.75 | O | CH₃ | H | CH₃ | H | OCF₃ | OH |
| Ia1.76 | O | H | H | CH₃ | CH₃ | SCH₃ | OH |
| Ia1.77 | O | H | H | CH₃ | CH₃ | SCH₂CH₃ | OH |
| Ia1.78 | O | H | H | CH₃ | CH₃ | SO₂CH₃ | OH |
| Ia1.79 | O | H | H | CH₃ | CH₃ | SO₂CH₂CH₃ | OH |
| Ia1.80 | O | H | H | CH₃ | CH₃ | SO₂CH(CH₃)₂ | OH |
| Ia1.81 | O | H | H | CH₃ | CH₃ | SO₂(CH₂)₂CH₃ | OH |
| Ia1.82 | O | H | H | CH₃ | CH₃ | Cl | OH |
| Ia1.83 | O | H | H | CH₃ | CH₃ | Br | OH |
| Ia1.84 | O | H | H | CH₃ | CH₃ | NO₂ | OH |
| Ia1.85 | O | H | H | CH₃ | CH₃ | CHF₂ | OH |
| Ia1.86 | O | H | H | CH₃ | CH₃ | CF₃ | OH |
| Ia1.87 | O | H | H | CH₃ | CH₃ | OCH₃ | OH |
| Ia1.88 | O | H | H | CH₃ | CH₃ | OCH₂CH₃ | OH |
| Ia1.89 | O | H | H | CH₃ | CH₃ | OCHF₂ | OH |
| Ia1.90 | O | H | H | CH₃ | CH₃ | OCF₃ | OH |
| Ia1.91 | O | CH₃ | CH₃ | CH₃ | H | SCH₃ | OH |
| Ia1.92 | O | CH₃ | CH₃ | CH₃ | H | SCH₂CH₃ | OH |
| Ia1.93 | O | CH₃ | CH₃ | CH₃ | H | SO₂CH₃ | OH |
| Ia1.94 | O | CH₃ | CH₃ | CH₃ | H | SO₂CH₂CH₃ | OH |
| Ia1.95 | O | CH₃ | CH₃ | CH₃ | H | SO₂CH(CH₃)₂ | OH |
| Ia1.96 | O | CH₃ | CH₃ | CH₃ | H | SO₂(CH₂)₂CH₃ | OH |
| Ia1.97 | O | CH₃ | CH₃ | CH₃ | H | Cl | OH |
| Ia1.98 | O | CH₃ | CH₃ | CH₃ | H | Br | OH |
| Ia1.99 | O | CH₃ | CH₃ | CH₃ | H | NO₂ | OH |
| Ia1.100 | O | CH₃ | CH₃ | CH₃ | H | CHF₂ | OH |
| Ia1.101 | O | CH₃ | CH₃ | CH₃ | H | CF₃ | OH |
| Ia1.102 | O | CH₃ | CH₃ | CH₃ | H | OCH₃ | OH |
| Ia1.103 | O | CH₃ | CH₃ | CH₃ | H | OCH₂CH₃ | OH |
| Ia1.104 | O | CH₃ | CH₃ | CH₃ | H | OCHF₂ | OH |
| Ia1.105 | O | CH₃ | CH₃ | CH₃ | H | OCF₃ | OH |
| Ia1.106 | O | CH₃ | H | CH₃ | CH₃ | SCH₃ | OH |
| Ia1.107 | O | CH₃ | H | CH₃ | CH₃ | SCH₂CH₃ | OH |
| Ia1.108 | O | CH₃ | H | CH₃ | CH₃ | SO₂CH₃ | OH |
| Ia1.109 | O | CH₃ | H | CH₃ | CH₃ | SO₂CH₂CH₃ | OH |
| Ia1.110 | O | CH₃ | H | CH₃ | CH₃ | SO₂CH(CH₃)₂ | OH |
| Ia1.111 | O | CH₃ | H | CH₃ | CH₃ | SO₂(CH₂)₂CH₃ | OH |
| Ia1.112 | O | CH₃ | H | CH₃ | CH₃ | Cl | OH |
| Ia1.113 | O | CH₃ | H | CH₃ | CH₃ | Br | OH |
| Ia1.114 | O | CH₃ | H | CH₃ | CH₃ | NO₂ | OH |
| Ia1.115 | O | CH₃ | H | CH₃ | CH₃ | CHF₂ | OH |
| Ia1.116 | O | CH₃ | H | CH₃ | CH₃ | CF₃ | OH |
| Ia1.117 | O | CH₃ | H | CH₃ | CH₃ | OCH₃ | OH |
| Ia1.118 | O | CH₃ | H | CH₃ | CH₃ | OCH₂CH₃ | OH |
| Ia1.119 | O | CH₃ | H | CH₃ | CH₃ | OCHF₂ | OH |
| Ia1.120 | O | CH₃ | H | CH₃ | CH₃ | OCF₃ | OH |
| Ia1.121 | O | CH₃ | CH₃ | CH₃ | CH₃ | SCH₃ | OH |
| Ia1.122 | O | CH₃ | CH₃ | CH₃ | CH₃ | SCH₂CH₃ | OH |
| Ia1.123 | O | CH₃ | CH₃ | CH₃ | CH₃ | SO₂CH₃ | OH |
| Ia1.124 | O | CH₃ | CH₃ | CH₃ | CH₃ | SO₂CH₂CH₃ | OH |
| Ia1.125 | O | CH₃ | CH₃ | CH₃ | CH₃ | SO₂CH(CH₃)₂ | OH |
| Ia1.126 | O | CH₃ | CH₃ | CH₃ | CH₃ | SO₂(CH₂)₂CH₃ | OH |
| Ia1.127 | O | CH₃ | CH₃ | CH₃ | CH₃ | Cl | OH |
| Ia1.128 | O | CH₃ | CH₃ | CH₃ | CH₃ | Br | OH |
| Ia1.129 | O | CH₃ | CH₃ | CH₃ | CH₃ | NO₂ | OH |
| Ia1.130 | O | CH₃ | CH₃ | CH₃ | CH₃ | CHF₂ | OH |
| Ia1.131 | O | CH₃ | CH₃ | CH₃ | CH₃ | CF₃ | OH |
| Ia1.132 | O | CH₃ | CH₃ | CH₃ | CH₃ | OCH₃ | OH |
| Ia1.133 | O | CH₃ | CH₃ | CH₃ | CH₃ | OCH₂CH₃ | OH |
| Ia1.134 | O | CH₃ | CH₃ | CH₃ | CH₃ | OCHF₂ | OH |
| Ia1.135 | O | CH₃ | CH₃ | CH₃ | CH₃ | OCF₃ | OH |
| Ia1.136 | O | CH₂Cl | H | H | H | SCH₃ | OH |
| Ia1.137 | O | CH₂Cl | H | H | H | SCH₂CH₃ | OH |
| Ia1.138 | O | CH₂Cl | H | H | H | SO₂CH₃ | OH |
| Ia1.139 | O | CH₂Cl | H | H | H | SO₂CH₂CH₃ | OH |
| Ia1.140 | O | CH₂Cl | H | H | H | SO₂CH(CH₃)₂ | OH |
| Ia1.141 | O | CH₂Cl | H | H | H | SO₂(CH₂)₂CH₃ | OH |
| Ia1.142 | O | CH₂Cl | H | H | H | Cl | OH |
| Ia1.143 | O | CH₂Cl | H | H | H | Br | OH |
| Ia1.144 | O | CH₂Cl | H | H | H | NO₂ | OH |
| Ia1.145 | O | CH₂Cl | H | H | H | CHF₂ | OH |
| Ia1.146 | O | CH₂Cl | H | H | H | CF₃ | OH |
| Ia1.147 | O | CH₂Cl | H | H | H | OCH₃ | OH |
| Ia1.148 | O | CH₂Cl | H | H | H | OCH₂CH₃ | OH |
| Ia1.149 | O | CH₂Cl | H | H | H | OCHF₂ | OH |
| Ia1.150 | O | CH₂Cl | H | H | H | OCF₃ | OH |
| Ia1.151 | NCH₃ | H | H | H | H | SCH₃ | OH |
| Ia1.152 | NCH₃ | H | H | H | H | SCH₂CH₃ | OH |
| Ia1.153 | NCH₃ | H | H | H | H | SO₂CH₃ | OH |
| Ia1.154 | NCH₃ | H | H | H | H | SO₂CH₂CH₃ | OH |
| Ia1.155 | NCH₃ | H | H | H | H | SO₂CH(CH₃)₂ | OH |
| Ia1.156 | NCH₃ | H | H | H | H | SO₂(CH₂)₂CH₃ | OH |
| Ia1.157 | NCH₃ | H | H | H | H | Cl | OH |
| Ia1.158 | NCH₃ | H | H | H | H | Br | OH |
| Ia1.159 | NCH₃ | H | H | H | H | NO₂ | OH |
| Ia1.160 | NCH₃ | H | H | H | H | CHF₂ | OH |
| Ia1.161 | NCH₃ | H | H | H | H | CF₃ | OH |
| Ia1.162 | NCH₃ | H | H | H | H | OCH₃ | OH |
| Ia1.163 | NCH₃ | H | H | H | H | OCH₂CH₃ | OH |
| Ia1.164 | NCH₃ | H | H | H | H | OCHF₂ | OH |
| Ia1.165 | NCH₃ | H | H | H | H | OCF₃ | OH |
| Ia1.166 | NCH₃ | CH₃ | H | H | H | SCH₃ | OH |
| Ia1.167 | NCH₃ | CH₃ | H | H | H | SCH₂CH₃ | OH |
| Ia1.168 | NCH₃ | CH₃ | H | H | H | SO₂CH₃ | OH |
| Ia1.169 | NCH₃ | CH₃ | H | H | H | SO₂CH₂CH₃ | OH |
| Ia1.170 | NCH₃ | CH₃ | H | H | H | SO₂CH(CH₃)₂ | OH |
| Ia1.171 | NCH₃ | CH₃ | H | H | H | SO₂(CH₂)₂CH₃ | OH |
| Ia1.172 | NCH₃ | CH₃ | H | H | H | Cl | OH |
| Ia1.173 | NCH₃ | CH₃ | H | H | H | Br | OH |
| Ia1.174 | NCH₃ | CH₃ | H | H | H | NO₂ | OH |
| Ia1.175 | NCH₃ | CH₃ | H | H | H | CHF₂ | OH |
| Ia1.176 | NCH₃ | CH₃ | H | H | H | CF₃ | OH |
| Ia1.177 | NCH₃ | CH₃ | H | H | H | OCH₃ | OH |
| Ia1.178 | NCH₃ | CH₃ | H | H | H | OCH₂CH₃ | OH |
| Ia1.179 | NCH₃ | CH₃ | H | H | H | OCHF₂ | OH |
| Ia1.180 | NCH₃ | CH₃ | H | H | H | OCF₃ | OH |
| Ia1.181 | NCH₃ | H | H | CH₃ | H | SCH₃ | OH |
| Ia1.182 | NCH₃ | H | H | CH₃ | H | SCH₂CH₃ | OH |
| Ia1.183 | NCH₃ | H | H | CH₃ | H | SO₂CH₃ | OH |
| Ia1.184 | NCH₃ | H | H | CH₃ | H | SO₂CH₂CH₃ | OH |
| Ia1.185 | NCH₃ | H | H | CH₃ | H | SO₂CH(CH₃)₂ | OH |
| Ia1.186 | NCH₃ | H | H | CH₃ | H | SO₂(CH₂)₂CH₃ | OH |
| Ia1.187 | NCH₃ | H | H | CH₃ | H | Cl | OH |
| Ia1.188 | NCH₃ | H | H | CH₃ | H | Br | OH |
| Ia1.189 | NCH₃ | H | H | CH₃ | H | NO₂ | OH |
| Ia1.190 | NCH₃ | H | H | CH₃ | H | CHF₂ | OH |
| Ia1.191 | NCH₃ | H | H | CH₃ | H | CF₃ | OH |
| Ia1.192 | NCH₃ | H | H | CH₃ | H | OCH₃ | OH |
| Ia1.193 | NCH₃ | H | H | CH₃ | H | OCH₂CH₃ | OH |
| Ia1.194 | NCH₃ | H | H | CH₃ | H | OCHF₂ | OH |

TABLE 1-continued

| No. | X | $R^2$ | $R^3$ | $R^4$ | $R^5$ | $R^6$ | $R^7$ |
|---|---|---|---|---|---|---|---|
| Ia1.195 | $NCH_3$ | H | H | $CH_3$ | H | $OCF_3$ | OH |
| Ia1.196 | $NCH_3$ | $CH_3$ | $CH_3$ | H | H | $SCH_3$ | OH |
| Ia1.197 | $NCH_3$ | $CH_3$ | $CH_3$ | H | H | $SCH_2CH_3$ | OH |
| Ia1.198 | $NCH_3$ | $CH_3$ | $CH_3$ | H | H | $SO_2CH_3$ | OH |
| Ia1.199 | $NCH_3$ | $CH_3$ | $CH_3$ | H | H | $SO_2CH_2CH_3$ | OH |
| Ia1.200 | $NCH_3$ | $CH_3$ | $CH_3$ | H | H | $SO_2CH(CH_3)_2$ | OH |
| Ia1.201 | $NCH_3$ | $CH_3$ | $CH_3$ | H | H | $SO_2(CH_2)_2CH_3$ | OH |
| Ia1.202 | $NCH_3$ | $CH_3$ | $CH_3$ | H | H | Cl | OH |
| Ia1.203 | $NCH_3$ | $CH_3$ | $CH_3$ | H | H | Br | OH |
| Ia1.204 | $NCH_3$ | $CH_3$ | $CH_3$ | H | H | $NO_2$ | OH |
| Ia1.205 | $NCH_3$ | $CH_3$ | $CH_3$ | H | H | $CHF_2$ | OH |
| Ia1.206 | $NCH_3$ | $CH_3$ | $CH_3$ | H | H | $CF_3$ | OH |
| Ia1.207 | $NCH_3$ | $CH_3$ | $CH_3$ | H | H | $OCH_3$ | OH |
| Ia1.208 | $NCH_3$ | $CH_3$ | $CH_3$ | H | H | $OCH_2CH_3$ | OH |
| Ia1.209 | $NCH_3$ | $CH_3$ | $CH_3$ | H | H | $OCHF_2$ | OH |
| Ia1.210 | $NCH_3$ | $CH_3$ | $CH_3$ | H | H | $OCF_3$ | OH |
| Ia1.211 | $NCH_3$ | $CH_3$ | H | $CH_3$ | H | $SCH_3$ | OH |
| Ia1.212 | $NCH_3$ | $CH_3$ | H | $CH_3$ | H | $SCH_2CH_3$ | OH |
| Ia1.213 | $NCH_3$ | $CH_3$ | H | $CH_3$ | H | $SO_2CH_3$ | OH |
| Ia1.214 | $NCH_3$ | $CH_3$ | H | $CH_3$ | H | $SO_2CH_2CH_3$ | OH |
| Ia1.215 | $NCH_3$ | $CH_3$ | H | $CH_3$ | H | $SO_2CH(CH_3)_2$ | OH |
| Ia1.216 | $NCH_3$ | $CH_3$ | H | $CH_3$ | H | $SO_2(CH_2)_2CH_3$ | OH |
| Ia1.217 | $NCH_3$ | $CH_3$ | H | $CH_3$ | H | Cl | OH |
| Ia1.218 | $NCH_3$ | $CH_3$ | H | $CH_3$ | H | Br | OH |
| Ia1.219 | $NCH_3$ | $CH_3$ | H | $CH_3$ | H | $NO_2$ | OH |
| Ia1.220 | $NCH_3$ | $CH_3$ | H | $CH_3$ | H | $CHF_2$ | OH |
| Ia1.221 | $NCH_3$ | $CH_3$ | H | $CH_3$ | H | $CF_3$ | OH |
| Ia1.222 | $NCH_3$ | $CH_3$ | H | $CH_3$ | H | $OCH_3$ | OH |
| Ia1.223 | $NCH_3$ | $CH_3$ | H | $CH_3$ | H | $OCH_2CH_3$ | OH |
| Ia1.224 | $NCH_3$ | $CH_3$ | H | $CH_3$ | H | $OCHF_2$ | OH |
| Ia1.225 | $NCH_3$ | $CH_3$ | H | $CH_3$ | H | $OCF_3$ | OH |
| Ia1.226 | $NCH_3$ | H | H | $CH_3$ | $CH_3$ | $SCH_3$ | OH |
| Ia1.227 | $NCH_3$ | H | H | $CH_3$ | $CH_3$ | $SCH_2CH_3$ | OH |
| Ia1.228 | $NCH_3$ | H | H | $CH_3$ | $CH_3$ | $SO_2CH_3$ | OH |
| Ia1.229 | $NCH_3$ | H | H | $CH_3$ | $CH_3$ | $SO_2CH_2CH_3$ | OH |
| Ia1.230 | $NCH_3$ | H | H | $CH_3$ | $CH_3$ | $SO_2CH(CH_3)_2$ | OH |
| Ia1.231 | $NCH_3$ | H | H | $CH_3$ | $CH_3$ | $SO_2(CH_2)_2CH_3$ | OH |
| Ia1.232 | $NCH_3$ | H | H | $CH_3$ | $CH_3$ | Cl | OH |
| Ia1.233 | $NCH_3$ | H | H | $CH_3$ | $CH_3$ | Br | OH |
| Ia1.234 | $NCH_3$ | H | H | $CH_3$ | $CH_3$ | $NO_2$ | OH |
| Ia1.235 | $NCH_3$ | H | H | $CH_3$ | $CH_3$ | $CHF_2$ | OH |
| Ia1.236 | $NCH_3$ | H | H | $CH_3$ | $CH_3$ | $CF_3$ | OH |
| Ia1.237 | $NCH_3$ | H | H | $CH_3$ | $CH_3$ | $OCH_3$ | OH |
| Ia1.238 | $NCH_3$ | H | H | $CH_3$ | $CH_3$ | $OCH_2CH_3$ | OH |
| Ia1.239 | $NCH_3$ | H | H | $CH_3$ | $CH_3$ | $OCHF_2$ | OH |
| Ia1.240 | $NCH_3$ | H | H | $CH_3$ | $CH_3$ | $OCF_3$ | OH |
| Ia1.241 | $NCH_3$ | $CH_3$ | $CH_3$ | $CH_3$ | H | $SCH_3$ | OH |
| Ia1.242 | $NCH_3$ | $CH_3$ | $CH_3$ | $CH_3$ | H | $SCH_2CH_3$ | OH |
| Ia1.243 | $NCH_3$ | $CH_3$ | $CH_3$ | $CH_3$ | H | $SO_2CH_3$ | OH |
| Ia1.244 | $NCH_3$ | $CH_3$ | $CH_3$ | $CH_3$ | H | $SO_2CH_2CH_3$ | OH |
| Ia1.245 | $NCH_3$ | $CH_3$ | $CH_3$ | $CH_3$ | H | $SO_2CH(CH_3)_2$ | OH |
| Ia1.246 | $NCH_3$ | $CH_3$ | $CH_3$ | $CH_3$ | H | $SO_2(CH_2)_2CH_3$ | OH |
| Ia1.247 | $NCH_3$ | $CH_3$ | $CH_3$ | $CH_3$ | H | Cl | OH |
| Ia1.248 | $NCH_3$ | $CH_3$ | $CH_3$ | $CH_3$ | H | Br | OH |
| Ia1.249 | $NCH_3$ | $CH_3$ | $CH_3$ | $CH_3$ | H | $NO_2$ | OH |
| Ia1.250 | $NCH_3$ | $CH_3$ | $CH_3$ | $CH_3$ | H | $CHF_2$ | OH |
| Ia1.251 | $NCH_3$ | $CH_3$ | $CH_3$ | $CH_3$ | H | $CF_3$ | OH |
| Ia1.252 | $NCH_3$ | $CH_3$ | $CH_3$ | $CH_3$ | H | $OCH_3$ | OH |
| Ia1.253 | $NCH_3$ | $CH_3$ | $CH_3$ | $CH_3$ | H | $OCH_2CH_3$ | OH |
| Ia1.254 | $NCH_3$ | $CH_3$ | $CH_3$ | $CH_3$ | H | $OCHF_2$ | OH |
| Ia1.255 | $NCH_3$ | $CH_3$ | $CH_3$ | $CH_3$ | H | $OCF_3$ | OH |
| Ia1.256 | $NCH_3$ | $CH_3$ | H | $CH_3$ | $CH_3$ | $SCH_3$ | OH |
| Ia1.257 | $NCH_3$ | $CH_3$ | H | $CH_3$ | $CH_3$ | $SCH_2CH_3$ | OH |
| Ia1.258 | $NCH_3$ | $CH_3$ | H | $CH_3$ | $CH_3$ | $SO_2CH_3$ | OH |
| Ia1.259 | $NCH_3$ | $CH_3$ | H | $CH_3$ | $CH_3$ | $SO_2CH_2CH_3$ | OH |
| Ia1.260 | $NCH_3$ | $CH_3$ | H | $CH_3$ | $CH_3$ | $SO_2CH(CH_3)_2$ | OH |
| Ia1.261 | $NCH_3$ | $CH_3$ | H | $CH_3$ | $CH_3$ | $SO_2(CH_2)_2CH_3$ | OH |
| Ia1.262 | $NCH_3$ | $CH_3$ | H | $CH_3$ | $CH_3$ | Cl | OH |
| Ia1.263 | $NCH_3$ | $CH_3$ | H | $CH_3$ | $CH_3$ | Br | OH |
| Ia1.264 | $NCH_3$ | $CH_3$ | H | $CH_3$ | $CH_3$ | $NO_2$ | OH |
| Ia1.265 | $NCH_3$ | $CH_3$ | H | $CH_3$ | $CH_3$ | $CHF_2$ | OH |
| Ia1.266 | $NCH_3$ | $CH_3$ | H | $CH_3$ | $CH_3$ | $CF_3$ | OH |
| Ia1.267 | $NCH_3$ | $CH_3$ | H | $CH_3$ | $CH_3$ | $OCH_3$ | OH |
| Ia1.268 | $NCH_3$ | $CH_3$ | H | $CH_3$ | $CH_3$ | $OCH_2CH_3$ | OH |
| Ia1.269 | $NCH_3$ | $CH_3$ | H | $CH_3$ | $CH_3$ | $OCHF_2$ | OH |
| Ia1.270 | $NCH_3$ | $CH_3$ | H | $CH_3$ | $CH_3$ | $OCF_3$ | OH |
| Ia1.271 | $NCH_3$ | $CH_3$ | $CH_3$ | $CH_3$ | $CH_3$ | $SCH_3$ | OH |
| Ia1.272 | $NCH_3$ | $CH_3$ | $CH_3$ | $CH_3$ | $CH_3$ | $SCH_2CH_3$ | OH |
| Ia1.273 | $NCH_3$ | $CH_3$ | $CH_3$ | $CH_3$ | $CH_3$ | $SO_2CH_3$ | OH |
| Ia1.274 | $NCH_3$ | $CH_3$ | $CH_3$ | $CH_3$ | $CH_3$ | $SO_2CH_2CH_3$ | OH |
| Ia1.275 | $NCH_3$ | $CH_3$ | $CH_3$ | $CH_3$ | $CH_3$ | $SO_2CH(CH_3)_2$ | OH |
| Ia1.276 | $NCH_3$ | $CH_3$ | $CH_3$ | $CH_3$ | $CH_3$ | $SO_2(CH_2)_2CH_3$ | OH |
| Ia1.277 | $NCH_3$ | $CH_3$ | $CH_3$ | $CH_3$ | $CH_3$ | Cl | OH |
| Ia1.278 | $NCH_3$ | $CH_3$ | $CH_3$ | $CH_3$ | $CH_3$ | Br | OH |
| Ia1.279 | $NCH_3$ | $CH_3$ | $CH_3$ | $CH_3$ | $CH_3$ | $NO_2$ | OH |
| Ia1.280 | $NCH_3$ | $CH_3$ | $CH_3$ | $CH_3$ | $CH_3$ | $CHF_2$ | OH |
| Ia1.281 | $NCH_3$ | $CH_3$ | $CH_3$ | $CH_3$ | $CH_3$ | $CF_3$ | OH |
| Ia1.282 | $NCH_3$ | $CH_3$ | $CH_3$ | $CH_3$ | $CH_3$ | $OCH_3$ | OH |
| Ia1.283 | $NCH_3$ | $CH_3$ | $CH_3$ | $CH_3$ | $CH_3$ | $OCH_2CH_3$ | OH |
| Ia1.284 | $NCH_3$ | $CH_3$ | $CH_3$ | $CH_3$ | $CH_3$ | $OCHF_2$ | OH |
| Ia1.285 | $NCH_3$ | $CH_3$ | $CH_3$ | $CH_3$ | $CH_3$ | $OCF_3$ | OH |
| Ia1.286 | $NCH_3$ | $CH_2Cl$ | H | H | H | $SCH_3$ | OH |
| Ia1.287 | $NCH_3$ | $CH_2Cl$ | H | H | H | $SCH_2CH_3$ | OH |
| Ia1.288 | $NCH_3$ | $CH_2Cl$ | H | H | H | $SO_2CH_3$ | OH |
| Ia1.289 | $NCH_3$ | $CH_2Cl$ | H | H | H | $SO_2CH_2CH_3$ | OH |
| Ia1.290 | $NCH_3$ | $CH_2Cl$ | H | H | H | $SO_2CH(CH_3)_2$ | OH |
| Ia1.291 | $NCH_3$ | $CH_2Cl$ | H | H | H | $SO_2(CH_2)_2CH_3$ | OH |
| Ia1.292 | $NCH_3$ | $CH_2Cl$ | H | H | H | Cl | OH |
| Ia1.293 | $NCH_3$ | $CH_2Cl$ | H | H | H | Br | OH |
| Ia1.294 | $NCH_3$ | $CH_2Cl$ | H | H | H | $NO_2$ | OH |
| Ia1.295 | $NCH_3$ | $CH_2Cl$ | H | H | H | $CHF_2$ | OH |
| Ia1.296 | $NCH_3$ | $CH_2Cl$ | H | H | H | $CF_3$ | OH |
| Ia1.297 | $NCH_3$ | $CH_2Cl$ | H | H | H | $OCH_3$ | OH |
| Ia1.298 | $NCH_3$ | $CH_2Cl$ | H | H | H | $OCH_2CH_3$ | OH |
| Ia1.299 | $NCH_3$ | $CH_2Cl$ | H | H | H | $OCHF_2$ | OH |
| Ia1.300 | $NCH_3$ | $CH_2Cl$ | H | H | H | $OCF_3$ | OH |

Extraordinary preference is also given to the compounds of the formula Ia2, in particular to the compounds Ia2.1 to Ia2.300, which differ from the corresponding compounds Ia1.1 to Ia1.300 in that $R^{11}$ is methyl.

Ia2

Extraordinary preference is also given to the compounds of the formula Ia3, in particular to the compounds Ia3.1 to Ia3.300, which differ from the compounds Ia1.1 to Ia1.300 in that $R^8$ is ethyl.

Ia3

Extraordinary preference is also given to the compounds of the formula Ia4, in particular to the compounds Ia4.1 to Ia4.300, which differ from the compounds Ia1.1 to Ia1.300 in that $R^8$ is ethyl and $R^{11}$ is methyl.

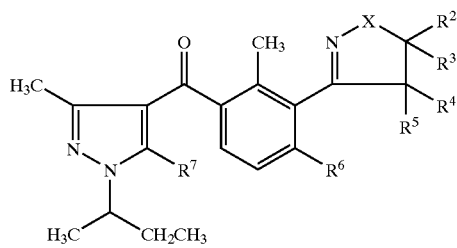

Ia4

Extraordinary preference is also given to the compounds of the formula Ia5, in particular to the compounds Ia5.1 to Ia5.300, which differ from the compounds Ia1.1 to Ia1.300 in that $R^8$ is 1-methyl-1-ethyl.

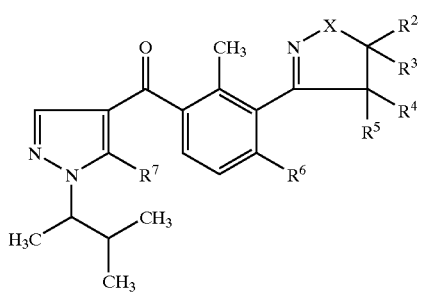

Ia5

Extraordinary preference is also given to the compounds of the formula Ia6, in particular to the compounds Ia6.1 to Ia6.300, which differ from the compounds Ia1.1 to Ia1.300 in that $R^8$ is 1-methyl-1-ethyl and $R^{11}$ is methyl.

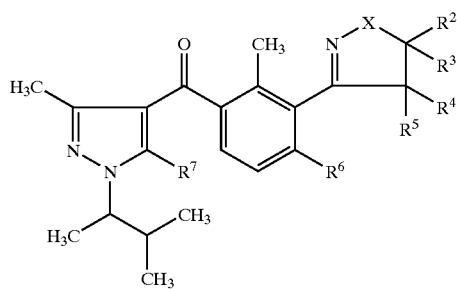

Ia6

Extraordinary preference is also given to the compounds of the formula Ia7, in particular to the compounds Ia7.1 to Ia7.300, which differ from the compounds Ia1.1 to Ia1.300 in that $R^{10}$ is methyl.

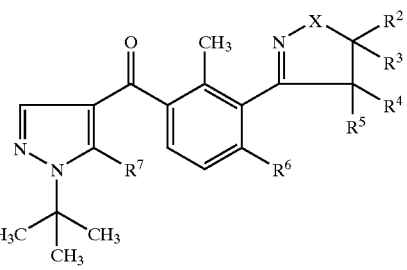

Ia7

Extraordinary preference is also given to the compounds of the formula Ia8, in particular to the compounds Ia8.1 to Ia8.300, which differ from the compounds Ia1.1 to Ia1.300 in that $R^{10}$ is methyl and $R^{11}$ is methyl.

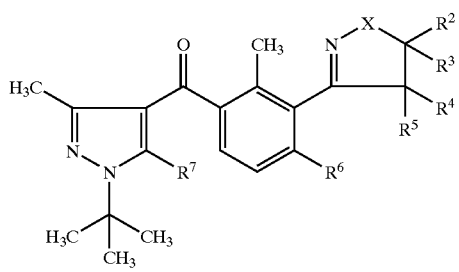

Ia8

Extraordinary preference is also given to the compounds of the formula Ia9, in particular to the compounds Ia9.1 to Ia9.300, which differ from the compounds Ia1.1 to Ia1.300 in that $R^8$ and $R^9$ are 1-methyl-1-ethyl.

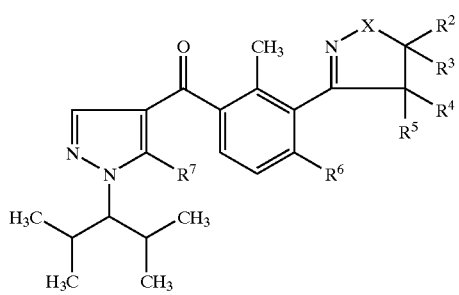

Ia9

Extraordinary preference is also given to the compounds of the formula Ia10, in particular to the compounds Ia10.1 to Ia10.300, which differ from the compounds Ia1.1 to Ia1.300 in that $R^8$ and $R^9$ are 1-methyl-1-ethyl and $R^{11}$ is methyl.

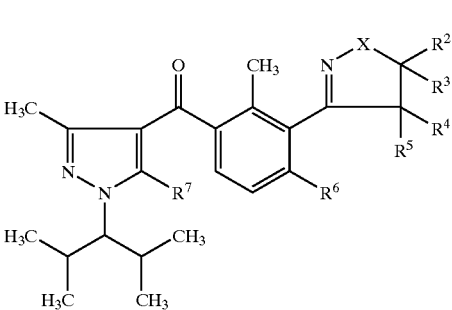

Ia10

Extraordinary preference is also given to the compounds of the formula Ia11, in particular to the compounds Ia11.1 to Ia.11.300, which differ from the compounds Ia1.1 to Ia1.300 in that $R^8$ is ethyl and $R^{10}$ is methyl.

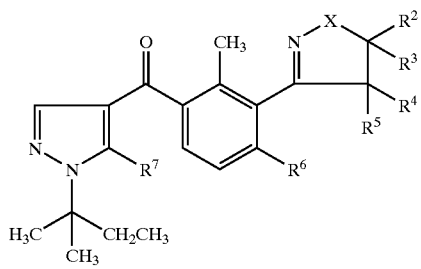

Ia11

Extraordinary preference is also given to the compounds of the formula Ia12, in particular to the compounds Ia12.1 to Ia12.300, which differ from the compounds Ia1.1 to Ia1.300 in that $R^8$ is ethyl and $R^{10}$ and $R^{11}$ are methyl.

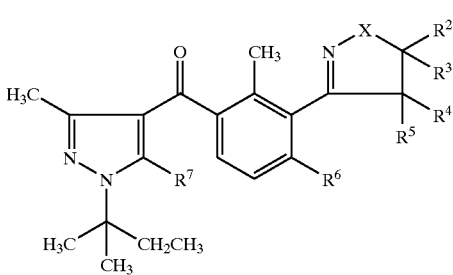

Ia12

The 3-(heterocyclyl)-substituted benzoylpyrazoles of the formula I can be obtained by various routes, for example by the processes below.

Process A:

Reaction of pyrazoles of the formula II with an activated benzoic acid IIIα or a benzoic acid IIIβ, which is preferably activated in situ, to give the corresponding acylation product IV, followed by rearrangement, gives compounds of the formula I where $R^7$=OH.

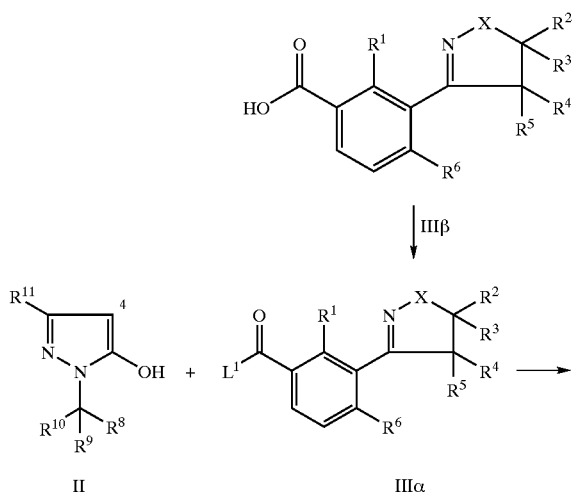

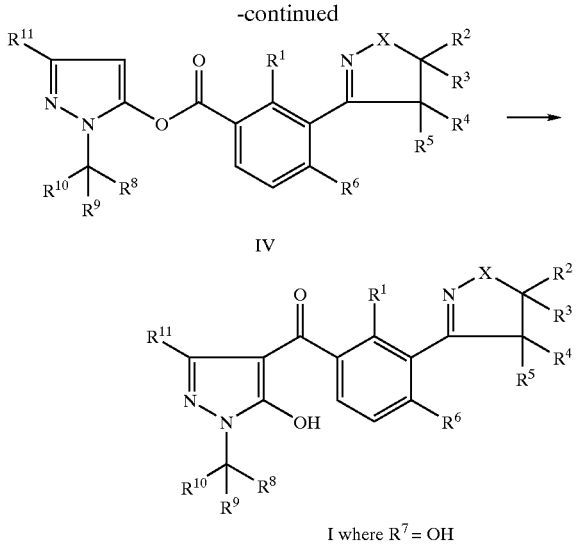

I where $R^7$ = OH $L^1$ is a nucleophilically replaceable leaving group, such as halogen, for example bromine, chlorine, hetaryl, for example imidazolyl, pyridyl, carboxylate, for example acetate, trifluoroacetate etc.

The activated benzoic acid can be employed directly, such as in the case of the benzoyl halides, or be generated in situ, for example using dicyclohexylcarbodiimide, triphenylphosphine/azodicarboxylic ester, 2-pyridine disulfide/triphenylphosphine, carbonyldiimidazole, etc.

It may be advantageous to carry out the acylation reaction in the presence of a base. The reactants and the auxiliary base are advantageously employed in equimolar amounts. A slight excess of auxiliary base, for example from 1.2 to 1.5 molar equivalents, based on II, may be advantageous in certain cases.

Suitable auxiliary bases are tertiary alkylamines, pyridine or alkali metal carbonates. Suitable for use as solvents are, for example, chlorinated hydrocarbons, such as methylene chloride, 1,2-dichloroethane, aromatic hydrocarbons, such as toluene, xylene, chlorobenzene, ethers, such as diethyl ether, methyl tert-butyl ether, dimethoxyethane, tetrahydrofuran, dioxane, polar aprotic solvents, such as acetonitrile, dimethylformamide, dimethyl sulfoxide, or esters, such as ethyl acetate, or mixtures of these.

If the activated carboxylic acid component used is a benzoyl halide, it may be advantageous to cool the reaction mixture to 0–10° C. when adding this reaction partner. The mixture is subsequently stirred at 20–100° C., preferably at 25–50° C., until the reaction has ended. Work-up is carried out in a customary manner, for example by pouring the reaction mixture into water and extracting the product of value. Solvents which are particularly suitable for this purpose are methylene chloride, diethyl ether, dimethoxyethane and ethyl acetate. The organic phase is dried and the solvent is removed, after which the crude ester can be employed for the rearrangement without any further purification.

The rearrangement of the esters to the compounds of the formula I is advantageously carried out at 20 –40° C in a solvent and in the presence of a base and, if appropriate, using a cyano compound as catalyst.

Suitable solvents are, for example, acetonitrile, methylene chloride, 1,2-dichloroethane, dioxane, ethyl acetate, dimethoxyethane, toluene or mixtures of these. Preferred solvents are acetonitrile and dioxane.

Suitable bases are tertiary amines, such as triethylamine or pyridine, or alkali metal carbonates, such as sodium carbonate or potassium carbonate, which are preferably employed in an equimolar amount or an up to four-fold excess, based on the ester. Preference is given to using triethylamine or alkali metal carbonates, preferably in twice the equimolar amount, based on the ester.

Suitable cyano compounds are inorganic cyanides, such as sodium cyanide and potassium cyanide, and organic cyano compounds, such as acetonecyanohydrine and trimethylsilyl cyanide. They are employed in an amount of from 1 to 50 mol percent, based on the ester. Preference is given to using acetonecyanohydrine or trimethylsilyl cyanide, for example in an amount of from 5 to 15, preferably 10, mol percent, based on the ester.

Work-up can be carried out in the manner known per se. The reaction mixture is, for example, acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, and the mixture is dried and concentrated. (Examples for the preparation of esters of hydroxypyrazoles and for the rearrangement of the esters are given, for example, in EP-A 282 944 and U.S. Pat No. 4,643,757).

However, it is also possible to generate the "acylation product" IV in situ by reacting a pyrazole of the formula II, or an alkali metal salt thereof, with a 3-(heterocyclyl)benzene derivative of the formula V in the presence of carbon monoxide, a catalyst and a base.

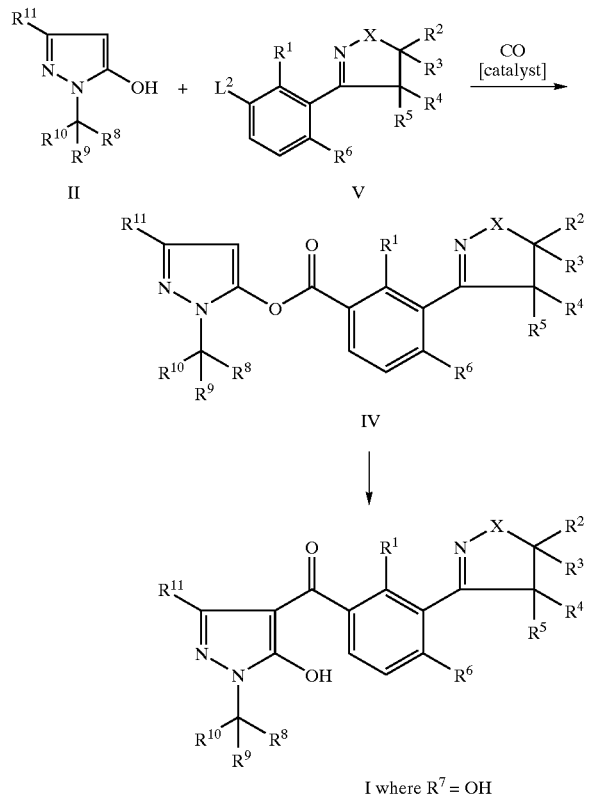

$L^2$ is a leaving group, such as halogen, for example chlorine, bromine or iodine, or sulfonate, such as mesylate or triflate; preference is given to bromine or triflate.

The "acylation product" IV proceeds to react, directly or indirectly, to give the 3-(heterocyclyl)-substituted benzoylpyrazole of the formula I.

Suitable catalysts are palladium-ligand complexes in which the palladium is present in oxidation state 0, metallic palladium, which has optionally been absorbed on a carrier, and preferably palladium(II) salts. The reaction with palladium(II) salts and metallic palladium is preferably carried out in the presence of complex ligands.

An example of a suitable palladium(0)-ligand complex is tetrakis(triphenylphosphine)palladium.

Metallic palladium is preferably absorbed on an inert carrier such as, for example, activated carbon, silica, alumina, barium sulfate or calcium carbonate. The reaction is preferably carried out in the presence of complex ligands such as, for example, triphenylphosphine.

Examples of suitable palladium(II) salts are palladium acetate and palladium chloride. The presence of complex ligands such as, for example, triphenylphosphine is preferred.

Suitable complex ligands for the palladium-ligand complexes, or in whose presence the reaction is preferably carried out with metallic palladium or palladium(II) salts, are tertiary phosphines whose structure is represented by the following formulae:

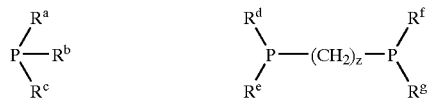

where z is 1 to 4 and the radicals $R^a$ to $R^g$ are $C_1$–$C_6$-alkyl, $C_3$–$C_6$-cycloalkyl, aryl-$C_1$-C2-alkyl or, preferably, aryl. Aryl is, for example, naphthyl and unsubstituted or substituted phenyl such as, for example, 2-tolyl and, in particular, unsubstituted phenyl.

The complex palladium salts can be prepared in a manner known per se starting from commercially available palladium salts such as palladium chloride or palladium acetate and the appropriate phosphines such as, for example, triphenylphosphine or 1,2-bis(diphenylphosphino)ethane. Many of the complexed palladium salts are also commercially available. Preferred palladium salts are [(R)(+)2,2', -bis(diphenylphosphino)-1,1'-binaphthyl]-palladium(II) chloride, bis(triphenylphosphine)palladium(II) acetate and, in particular, bis(triphenylphosphine)palladium(II) chloride.

The palladium catalyst is usually employed in a concentration of from 0.05 to 5 mol %, and preferably 1–3 mol %.

Suitable bases are tertiary amines, such as, for example, N-methylpiperidine, ethyldiisopropylamine, 1,8-bisdimethylaminonaphthalene or, in particular, triethylamine. Also suitable are alkali metal carbonates, such as sodium carbonate or potassium carbonate. However, mixtures of potassium carbonate and triethylamine are also suitable.

In general, from 2 to 4 molar equivalent, in particular 2 molar equivalents, of the alkali metal carbonate, and from 1 to 4 molar equivalents, in particular 2 molar equivalents, of the tertiary amine are employed, based on the 3-(heterocyclyl)-benzene derivatives of the formula V.

Suitable solvents are nitriles, such as benzonitrile and acetonitrile, amides, such as dimethylformamide, dimethylacetamide, tetra-$C_1$–$C_4$-alkylureas or N-methylpyrrolidone and, preferably, ethers, such as tetrahydrofuran and methyl tert-butyl ethers. Particular preference is given to ethers, such as 1,4-dioxane and dimethoxyethane.

Process B:

Compounds of the formula I where $R^7$ ≠hydroxyl are obtained by reacting compounds of the formula I where $R^7$=hydroxyl with alkylating agents, sulfonylating agents or acylating agents $L^3$-$R^{7a}$ (VI).

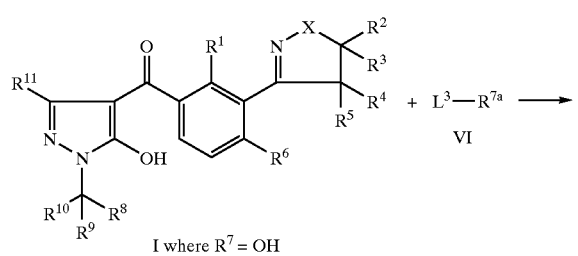

I where R⁷ = OH

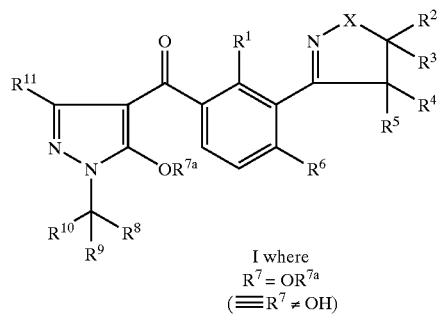

I where
R⁷ = OR⁷ᵃ
(≡R⁷ ≠ OH)

$L^3$ is a nucleophilically replaceable leaving group, such as halogen, for example bromine or chlorine, acyloxy, for example acetyloxy or ethylcarbonyloxy, or alkylsulfonyloxy, for example methylsulfonyloxy or trifluoromethylsulfonyloxy.

$R^{7a}$ is $C_1$–$C_6$-alkyl, $C_3$–$C_6$-alkenyl, $C_1$–$C_6$-alkylsulfonyl, $C_1$-$C_6$-alkylcarbonyl, $C_1$–$C_4$-(alkylthio)carbonyl, phenylsulfonyl or phenylcarbonyl, where the phenyl radical of the two last-mentioned substituents may be partially or fully halogenated and/or may carry one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy.

The compounds of the formula VI can be employed directly, such as, for example, in the case of the sulfonyl halides or sulfonic anhydrides, or be generated in situ, for example activated sulfonic acids (using sulfonic acid and dicyclohexylcarbonyldiimide, carbonyldiimidazole, etc.).

The starting materials are generally employed in equimolar amounts. However, it may also be advantageous to employ an excess of one or the other component.

If appropriate, it may be advantageous to carry out the reaction in the presence of a base. The reactants and the auxiliary base are advantageously employed in equimolar amounts. An excess of auxiliary base, for example from 1.5 to 3 molar equivalents, based on I, may be advantageous in certain cases.

Suitable auxiliary bases are tertiary alkylamines, such as triethylamine, pyridine, alkali metal carbonates, for example sodium carbonate or potassium carbonate, and alkali metal hydrides, for example sodium hydride. Preference is given to using triethylamine and pyridine.

Suitable solvents are, for example, chlorinated hydrocarbons, such as methylene chloride and 1,2-dichloroethane, aromatic hydrocarbons, for example toluene, xylene, chlorobenzene, ethers, such as diethyl ether, methyl tert-butyl ether, tetrahydrofuran and dioxane, polar aprotic solvents, such as acetonitrile, dimethylformamide, dimethyl sulfoxide, or esters, such as ethyl acetate, or mixtures of these.

In general, the reaction temperature is in the range from 0° C. to the boiling point of the reaction mixture.

Work-up can be carried out in the manner known per se to give the product.

The pyrazoles of the formula II used as starting materials are known or can be prepared by the process known per se (for example EP-A 240 001 and J. Prakt. Chem. 315, 383 (1973)).

The activated benzoic acids IIIα can be obtained in a manner known per se from the benzoic acids IIIβ. The latter for their part are obtained by hydrolysis from the corresponding esters VII. These can be prepared by converting an oxime or hydrazone of the formula VIII into the corresponding hydroxamic acid halide, in particular hydroxamic acid chloride, or carbohydrazide halide, in particular carbohydrazide chloride; generating a nitrile oxide or nitrile imine in situ and reacting this with an alkene (cf., for example, Chem. Ber. 106, 3258–3274 (1973)).

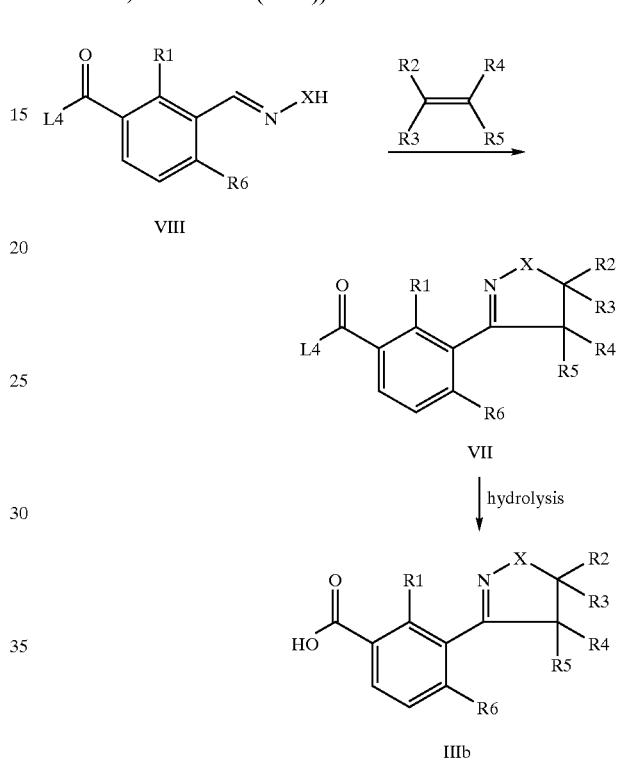

$L^4$ denotes a $C_1$–$C_6$-alkoxy radical.

However, the benzoic acids IIIβ can also be obtained by converting an oxime or hydrazine of the formula IX into the corresponding nitrile oxides or nitrile imines and reacting these with alkenes to give the corresponding cycloaddition products (cf., for example, Chem. Ber. 106, 3258–3274 (1973)). Thus, for example, the oxime of the formula IX (X=O) is oxidized with sodium hypochlorite and reacted with a suitable alkene in an inert solvent such as methylene chloride, chloroform, tetrahydrofuran, dioxane or acetonitrile. The product is then converted in the presence of a catalyst and a base into the benzoic acid IIIβ using carbon monoxide and water.

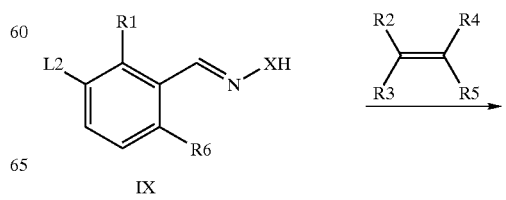

IX

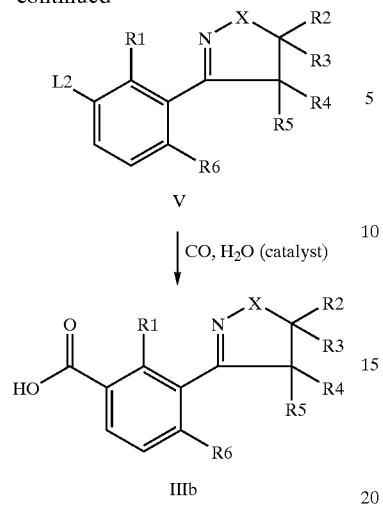

L² denotes a leaving group, such as halogen, for example chlorine, bromine or iodine, or sulfonate, such as mesylate or triflate, preferably bromine or triflate.

With respect to the carbonylation reaction, what has been said above applies analogously.

The compounds of the formulae III and V are in each case novel as such

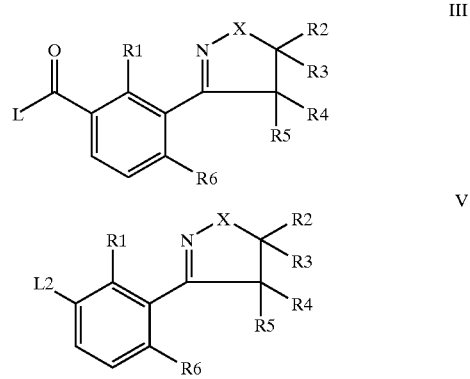

where in each case the variables $R^1$, $R^3$ to $R^6$ and X are as defined under the compounds of the formula I and $R^2$ is $C_1$–$C_4$-haloalkyl;

L is hydroxyl or a radical that can be removed by hydrolysis; or

L² is a leaving group that can be displaced nucleophilically.

Examples of radicals that can be removed by hydrolysis are alkoxy, phenoxy, alkylthio and phenylthio radicals, which may be unsubstituted or substituted, halides, hetaryl radicals attached via nitrogen, amino and imino radicals, which may be unsubstituted or substituted, etc.

Examples of nucleophilically displaceable leaving groups are halogen, $C_1$–$C_4$-alkylsulfonyloxy and $C_1$–$C_4$-haloalkylsulfonyloxy;

Preferred compounds of the formula III are those compounds in which L is halogen, in particular chlorine or bromine.

Preference is also given to those compounds of the formula III in which L is $C_1$–$C_6$-alkoxy.

Preference is also given to those compounds of the formula III in which L is hydroxyl.

With respect to the variables X, $R^1$ and $R^3$ to $R^6$, the particularly preferred embodiments of the compounds of the formulae III and V correspond to those of the compounds of the formula I.

PREPARATION EXAMPLES

4-[2-Methyl-3-(4,5-dihydroisoxazol-3-yl)-4-methylsulfonylbenzoyl)]-5-hydroxy-1-(1,1-dimethyl-1-ethyl)-1H-pyrazole (Compound 2.1)

Variant 1:

0.61 g (3.5 mmol) of 1-(1,1-dimethyl-1-ethyl)-5-hydroxy-1H-pyrazole and 0.79 g (3.9 mmol) of dicyclohexylcarbodiimide were added to a solution of 1.0 g (3.5 mmol) of 2-methyl-3-(4,5-dihydroisoxazol-3-yl)-4-methylsulfonylbenzoic acid in dioxane, and the mixture was stirred at room temperature for 12 hours. Insoluble components were separated off, and 0.58 g (4.2 mmol) of potassium carbonate was then added and the mixture was refluxed for 3 hours. The solvent was then distilled off, the residue was taken up in 5% strength potassium carbonate solution and washed with methylene chloride and toluene, the pH was adjusted to 3 using 10% strength hydrochloric acid and the mixture was extracted with methylene chloride. This methylene chloride solution was dried and the solvent was removed. This gave 0.81 g (57% of theory) of 4-[2-methyl-3-(4,5-dihydroisoxazol-3-yl)-4-methylsulfonylbenzoyll-5-hydroxy-1-(1,1-dimethyl-1-ethyl)-1H-pyrazole] M.p. 195–198° C.

Variant 2

3.78 g (32 mmol) of thionyl chloride were added to a solution of 6 g (21.2 mmol) of 2-methyl-3-(4,5-dihydroisoxazol-3-yl)-4-methylsulfonylbenzoic acid in toluene, and the mixture was refluxed for 4 hours. The solvent was removed, the residue was then taken up in dimethoxyethane and a solution of 2.97 g (21.2 mmol) of 1-(1, 1-dimethyl-1-ethyl)-5-hydroxy-1H-pyrazole in dimethoxyethane was added dropwise. The mixture was subsequently stirred at room temperature for 12 hours and refluxed for 3.5 hours. The reaction mixture was cooled, the solvent was distilled off, and the residue was taken up in 5% strength potassium carbonate solution and washed with methylene chloride. The resulting aqueous phase was adjusted to pH=1 using hydrochloric acid, and the resulting precipitate was filtered off with suction. This gave 4.89 g (52%) of 4-[2-methyl-3-(4,5-dihydroisoxazol-3-yl)-4-methylsulfonylbenzoyll-5-hydroxy-1-(1,1-dimethyl-1-ethyl)-1H-pyrazole] M.p. 195–198° C.

In addition to the compound above, Table 2 lists further 3-(heterocyclyl)-substituted benzoylpyrazoles of the formula I which were prepared or are preparable in a similar manner.

TABLE 2

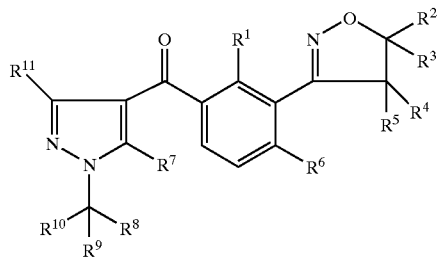

I where X = O

| No. | $R^1$ | $R^2$ | $R^3$ | $R^4$ | $R^5$ | $R^6$ | $R^7$ | $R^8$ | $R^9$ | $R^{10}$ | $R^{11}$ | physical data m.p. [° C.] $^1$H—NMR [δ in ppm] |
|---|---|---|---|---|---|---|---|---|---|---|---|---|
| 2.1 | $CH_3$ | H | H | H | H | $SO_2CH_3$ | OH | $CH_3$ | $CH_3$ | $CH_3$ | H | 195–198 |
| 2.2 | $CH_3$ | H | H | H | H | $SO_2CH_3$ | $OCH(CH_3)_2$ | $CH_3$ | $CH_3$ | $CH_3$ | H | oil |
| 2.3 | $CH_3$ | H | H | H | H | $SO_2CH_3$ | $OCO[3\text{-F}—C_6H_4]$ | $CH_3$ | $CH_3$ | $CH_3$ | H | 210–211 |
| 2.4 | $CH_3$ | H | H | H | H | $SO_2CH_3$ | $OCO[3,5\text{-}(CF_3)_2—C_6H_3]$ | $CH_3$ | $CH_3$ | $CH_3$ | H | oil |
| 2.5 | $CH_3$ | H | H | H | H | $SO_2CH_3$ | $OCO[2,4\text{-}F_2—C_6H_3]$ | $CH_3$ | $CH_3$ | $CH_3$ | H | 145–148 |
| 2.6 | $CH_3$ | H | H | H | H | $SO_2CH_3$ | $OCO[3,5\text{-}F_2—C_6H_3]$ | $CH_3$ | $CH_3$ | $CH_3$ | H | 100–105 |
| 2.7 | $CH_3$ | H | H | H | H | $SO_2CH_3$ | $OCO[3\text{-}(CF_3)—C_6H_4]$ | $CH_3$ | $CH_3$ | $CH_3$ | H | 90–93 |
| 2.8 | $CH_3$ | H | H | H | H | $SO_2CH_3$ | OH | $CH_3$ | $CH_3$ | $CH_3$ | $CH_3$ | 198–200 |
| 2.9 | $CH_3$ | H | H | H | H | $SO_2CH_3$ | OH | $CH_3$ | $CH_3$ | H | H | 203–205 |
| 2.10 | $CH_2—CH_3$ | H | H | H | H | $SO_2CH_3$ | OH | $CH_3$ | $CH_3$ | $CH_3$ | H | 75–80 |
| 2.11 | $CH_3$ | H | H | H | H | $SO_2CH_3$ | OH | $CH(CH_3)_2$ | $CH_3$ | H | H | 90–95 |
| 2.12 | $CH_3$ | H | H | H | H | $SO_2CH_3$ | $OCOC_6H_5$ | $CH(CH_3)_2$ | $CH_3$ | H | H | 95–100 |
| 2.13 | $CH_3$ | $CH_2Cl$ | H | H | H | $SO_2CH_3$ | OH | $CH_3$ | $CH_3$ | $CH_3$ | H | 80–81 |
| 2.14 | $CH_3$ | $CH_2Cl$ | H | H | H | $SO_2CH_3$ | OH | $CH_3$ | $CH_3$ | H | H | 75–84 |
| 2.15 | $CH_3$ | $CH_2Cl$ | H | H | H | $SO_2CH_3$ | $OCO[3\text{-F}—C_6H_4]$ | $CH_3$ | $CH_3$ | H | H | 77–83 |
| 2.16 | $CH_3$ | H | H | H | H | $SO_2CH_3$ | OH | $CH(CH_3)_2$ | $CH(CH_3)_2$ | H | H | 120–125 |
| 2.17 | $CH_3$ | $CH_2Cl$ | $CH_2Cl$ | H | H | $SO_2CH_3$ | OH | $CH_3$ | $CH_3$ | H | H | 73–79 |
| 2.18 | $CH_3$ | $CH_2Cl$ | $CH_2Cl$ | H | H | $SO_2CH_3$ | OH | $CH_3$ | $CH_3$ | $CH_3$ | H | 73–78 |
| 2.19 | $CH_3$ | H | H | H | H | $SO_2CH_3$ | $OCH_3$ | $CH_3$ | $CH_3$ | H | H | oil |
| 2.20 | $CH_3$ | H | H | H | H | $SO_2CH_3$ | $OCH_2CH_3$ | $CH_3$ | $CH_3$ | H | H | 165–170 |
| 2.21 | $CH_3$ | H | H | H | H | $SO_2CH_3$ | $OCH(CH_3)_2$ | $CH_3$ | $CH_3$ | H | H | oil |
| 2.22 | $CH_3$ | H | H | H | H | $SO_2CH_3$ | $OCOC_6H_5$ | $CH_3$ | $CH_3$ | H | H | oil |
| 2.23 | $CH_3$ | H | H | H | H | $SO_2CH_3$ | $OCO[3\text{-F}—C_6H_4]$ | $CH_3$ | $CH_3$ | H | H | 110–115 |
| 2.24 | $CH_3$ | H | H | H | H | $SO_2CH_3$ | $OCOCH_3$ | $CH_3$ | $CH_3$ | H | H | 80–85 |
| 2.25 | $CH_3$ | H | H | H | H | $SO_2CH_3$ | $OSO_2[4\text{-}CH_3—C_6H_4]$ | $CH_3$ | $CH_3$ | H | H | 95–100 |
| 2.26 | $CH_3$ | H | H | H | H | $SO_2CH_3$ | $OCOSCH_3$ | $CH_3$ | $CH_3$ | H | H | 143–145 |
| 2.27 | $CH_3$ | H | H | H | H | $SO_2CH_3$ | $OCOC_6H_5$ | $CH_3$ | $CH_3$ | $CH_3$ | H | 228–230 |

The 3-(heterocyclyl)-substituted benzoylpyrazoles of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against weeds and harmful grasses in crops such as wheat, rice, maize, soya and cotton without causing any significant damage to the crop plants. This effect is mainly observed at low rates of application.

Depending on the particular application method used, the compounds of the formula I, or the herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, broadcasting or watering. The use forms depend on the intended aims; in any case, they should guarantee a very fine distribution of the active compounds according to the invention.

The herbicidal compositions comprise a herbicidally effective amount of at least one compound of the formula I or an agriculturally useful salt of I and auxiliaries which are customarily used for formulating crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ether, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active compounds together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise about from 0.001 to 98% by weight, preferably 0.01 to 95% by weight, of at least one active compound. The active compounds are employed in a purity of from 90% to 100%, preferably 95% to 100% (according to the NMR spectrum).

The following formulation examples illustrate the preparation of such formulations:

I. 20 parts by weight of the compound No. 2.8 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 2.9 are dissolved in a mixture composed of 40 parts by weight of cyclohexanone, parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. 2.3 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. 2.3 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. 2.9 are mixed with 97 parts by weight of finely divided kaolin. This gives a dust which comprises 3% by weight of the active compound.

VI. 20 parts by weight of the active compound No. 2.8 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active compound No. 2.3 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active compound No. 2.9 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of the compound of the formula I are from 0.001 to 3.0, preferably 0.01 to 1.0, kg/ha of active substance (a.s.), depending on the control target, the season, the target plants and the growth stage.

To widen the activity spectrum and to achieve synergistic effects, the 3-(heterocyclyl)-substituted benzoylpyrazoles of the formula I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het) aryloxyalkanoic acids and their derivatives, benzoic acid and its derivatives, benzothiadiazinones, 2-(het)aroyl-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexeneone oxime ether derivatives, diazines, dichloropropionic acid and its derivatives, dihydrobenzofurans, dihydrofuran- 3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, 2-pyrimidyl ethers, sulfonamides, sulfonylureas, triazines, triazinones, triazolinones, triazolecarboxamides and uracils.

It may furthermore be advantageous to apply the compounds of the formula I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of the 3-(heterocyclyl)-substituted benzoylpyrazoles of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this has been adversely effected by the active compounds.

For the post-emergence treatment, the test plants were first grown to a height of 3 to 15 cm, depending on the plant habit, and only then treated with the active compounds which had been suspended or emulsified in water. The test plants were, for this purpose, either sown directly and grown in the same containers, or they were first grown separately as seedlings and transplanted into the test containers a few days prior to treatment. The application rate for the post-emergence treatment was 0.5, 0.25, 0.125 or 0.0625 kg of a.s. (active substance)/ha.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments were of the following species:

| Scientific name | Common name |
|---|---|
| Abutilon theophrasti | velvet leaf |
| Amaranthus retroflexus | pigweed |
| Avena fatua | wild oat |
| Chenopodium album | lamb's-quarters |
| Echinochloa crus galli | barnyard grass |
| Polygonum persicaria | lady's-thumb |
| Setaria faberi | giant foxtail |
| Setaria viridis | green foxtail |
| Sinapis alba | white mustard |
| Solanum nigrum | black nightshade |

At application rates of 0.125 or 0.0625 kg/ha, the compound 2.3 (Table 2) showed very good action against the undesirable plants barnyard grass, pigweed, lamb's-quarters, lady's-thumb and black nightshade when used in the post-emergence method.

Furthermore, compound 2.8 (Table 2) effected very good post-emergence control at application rates of 0.5 or 0.25 kg/ha of the harmful plants barnyard grass, green foxtail, lamb's-quarters and black nightshade.

The action of compound 2.9 (Table 2), when applied in the post-emergence method at application rates of 0.25 or 0.125 kg/ha, on the grasses wild oat and green foxtail and on the weeds pigweed, lady's-thumb and white mustard is very good.

Likewise, the compound 2.10 (Table 2) effects, at application rates of 0.25 or 0.125 kg/ha, very good post-emergence control of the undesirable plants barnyard grass, lamb's-quarters, white mustard and black nightshade.

We claim:

1. A 3-(heterocyclyl)-substituted benzoylpyrazole of the formula I

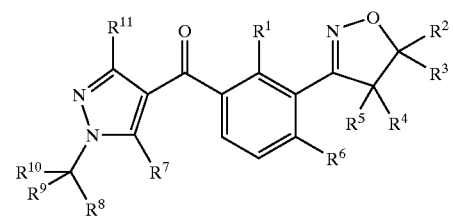

where:

X is O, NH or N($C_1$–$C_6$-alkyl);

$R^1$ is $C_1$–C6-alkyl;

$R^2$, $R^3$, $R^4$, $R^5$ are hydrogen, $C_1$–$C_4$-alkyl or $C_1$–$C_4$-haloalkyl;

$R^6$ is halogen, nitro, $C_1$–$C_4$-haloalkyl, $C_1$–$C_4$-alkoxy, $C_1$–C4-haloalkoxy, $C_1$–$C_4$-alkylthio, $C_1$–$C_4$-haloalkylthio, $C_1$–$C_4$-alkylsulfonyl or $C_1$–$C_4$-haloalkyloulfonyl;

$R^7$ is hydroxyl, $C_1$–$C_6$-alkoxy, $C_3$–$C_6$-alkenyloxy, $C_1$–$C_6$-alkylsulfonyloxy, $C_1$–C6-alkylcarbonyloxy, C–$C_4$-(alkylthio)carbonyloxy, phenylsultonyloxy or phenylcarbonyloxy, where the phenyl radical of the two last-mentioned substituents may be partially or fully halogenated and/or may carry one to three of the following groups:

nitro, cyano, $C_1$–C4-alkyl, $C_1$–$C_4$-haloalkyl, $C_1$–$C_4$-alkoxy or $C_1$–$C_4$-haloalkoxy;

$R^8$, $R^9$ are $C_1$–$C_4$-alkyl;

$R^{10}$ is hydrogen or $C_1$–$C_4$-alkyl;

where the number of the carbon atoms of the radicals $R^8$, $R^9$ and $R^{10}$ together is at most 7, $R^{11}$ is hydrogen or $C_1$–$C_4$-alkyl;

and its agriculturally useful salts.

2. A 3-(heterocyclyl)-substituted benzoylpyrazole of the formula I as claimed in claim 1 where X is O;

$R^1$ is $C_2$–$C_4$-alkyl;

$R^6$ is $C_1$–$C_4$-alkylthio or $C_1$–$C_4$-alkylsulfonyl.

3. A 3-(heterocyclyl)-substituted benzoylpyrazole of the formula I as claimed in claim 1 where X is O;

$R^1$ is $C_1$–$C_4$-alkyl;

$R^6$ is halogen nitro, $C_1$–$C_4$haloalkyl, $C_1$–$C_4$-alkoxy or $C_1$–$C_4$-haloalkoxy.

4. A 3-(heterocyclyl)-substituted benzoylpyrazole of the formula I as claimed in claim 1 where X is $N(C_1$–$C_6$-alkyl).

5. A process for preparing 3-(heterocyclyl)-substituted benzoylpyrazoles of the formula I as claimed in claim 1, which comprises acylating a pyrazole of the formula II

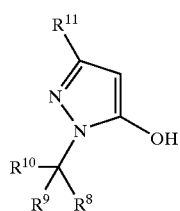

with an activated benzoic acid IIIα or a benzoic acid IIIβ,

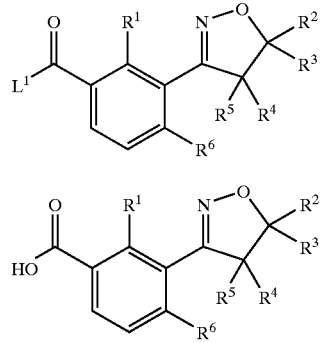

where the variables X, $R^1$ to $R^6$ and $R^8$ to $R^{11}$ are as defined in claim 1 and $L^1$ is a nucleophilically replaceable leaving group and rearranging the acylation product, in the presence or absence of a catalyst, to give the compounds of the formula I where $R^7$ is a hydroxyl and optionally, to prepare 3-(heterocyclyl)-substituted benzoylpyrazoles of formula I where $R^7$ is not hydroxyl as claimed in claim 1, reacting the obtained product with a compound of formula VI $$L^3-R^{7a} \qquad VI$$

wherein $L^3$ is a nucleophilically replaceable leaving group, and $R^{7a}$ is $C_1$–$C_6$-alkyl, $C_3$–$C_6$-alkenyl, $C_1$–$C_6$-alkylsulfonyl, $C_1$–$C_6$-alkylcarbonyl, $C_1$–$C_4$-(alkylthio)carbanyloxy, phenylsulfonyl or phenylcarbonyl, where the phenyl radical of the two last-mentioned substituents may be partially of fully halogenated and/or may carry one to three of the following groups; nitro, cyano, $C_1$–$C_4$-alkyl, $C_1$–$C_4$-haloalkyl, $C_1$–$C_4$-alkoxy or $C_1$–$C_4$-haloalkoxy.

6. A process for preparing 3-(heterocyclyl)-substituted benzoylpyrazoles of the formula I as claimed in claim 1, which comprises reacting a pyrazole of the formula II

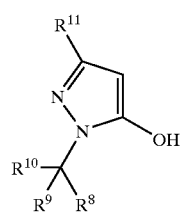

in which the variables $R^8$ to $R^{11}$ are as defined in claim 1, or an alkali metal salt thereof, with a 3-(heterocyclyl) benzene derivative of the formula V

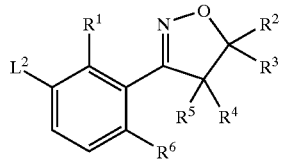

where the variables X and $R^1$ to $R^6$ are as defined in claim 1 and $L^2$ is a leaving group in the presence of carbon monoxide, a catalyst and a base, to give the compounds of formula I where $R^7$ is an hydroxyl and optionally, to prepare 3-(heterocyclyl)-substituted benzylpyrazoles of formula I were $R^7$ is not hydroxyl as claimed in claim 1, reacting the obtained product with a compound of formula VI $$L^3-R^{7a} \qquad VI$$

wherein $L^3$ is a nucleophilically replaceable leaving group, and $R^{7a}$ is $C_1$–$C_6$-alkyl, $C_3$–$C_6$-alkenyl, $C_1$–$C_6$-alkylsulfonyl, $C_1$–$C_6$-alkylcarbonyl, $C_1$–$C_4$-(alkylthio)carbonyloxy, phenylsulfonyl or phenylcarbonyl, where the phenyl radical of the two last-mentioned substituents may be partially of fully halogenated and/or may carry one to three of the following groups:

nitro, cyano, $C_1$–$C_4$-alkyl, $C_1$–$C_4$-haloalkyl, $C_1$–$C_4$-alkoxy or $C_1$–$C_4$-haloalkoxy.

7. A composition, comprising a herbicidally effective amount of at least one 3-(heterocyclyl)-substituted benzoylpyrazole of the formula I or an agriculturally useful salt of I as claimed in claim 1 and auxiliaries which are customarily used for formulating crop protection agents.

8. A method for controlling undesirable vegetation, characterized in that a herbicidally effective amount of at least one 3-(heterocyclyl)-substituted benzoylpyrazole of the formula I or an agriculturally useful salt of I as claimed in claim 1 is allowed to act on the plants, their habitat and/or on seed.

9. A process for preparing compositions as claimed in claim 7, which comprises mixing a herbicidally effective amount of at least one 3-(heterocyclyl)-substituted benzopyrazole or an agriculturally useful salt of the formula I is applied to plants, seeds and/or their habitat.

10. A 3-(heterocyclyl)-substituted benzoylpyrazole of formula I as defined in claim 1 wherein $R^7$ is hydroxyl, $C_1$–$C_6$-alkoxy, $C_3$–$C_6$-alkenyloxy, $C_1$–$C_6$-alkylsulfonyloxy, $C_1$–$C_6$-alkylcarbonyloxy, $C_1$–$C_6$- alkylthiocarbonyloxy or phenylcarbonyloxy, where the phenyl radical of the last-mentioned substituent may be partially or fully halogenated and/or may carry one to three of the following groups:
nitro, cyano, $C_1$–$C_4$-alkyl, $C_1$–$C_4$-haloalkyl, $C_1$–$C_4$-alkoxy or $C_1$–$C_4$-haloalkoxy.

11. A 3-(heterocyclyl)-substituted benzoylpyrazole of formula I as defined in claim 10, wherein X is O;

$R^1$ is $C_1$–$C_4$-alkyl;

$R^6$ is $C_1$–$C_4$-alkylthio or $C_1$–$C_4$-alkylsulfonyl.

12. A 3-(heterocyclyl)-substituted benzoylpyrazole of formula I as defined in claim 10 wherein X is O;

$R^1$ is $C_1$–$C_4$-alkyl;

$R^6$ is halogen, nitro, $C_1$–$C_4$-haloalkyl, $C_1$–$C_4$-alkoxy or $C_1$–$C_4$-haloalkoxy.

13. A 3-(heterocyclyl)-substituted benzoylpyrazole of formula I as defined in claim 10 wherein X is $N(C_1$–$C_6$-alkyl).

* * * * *

UNITED STATES PATENT AND TRADEMARK OFFICE
CERTIFICATE OF CORRECTION

PATENT NO. : 6,831,039 B1
DATED : December 14, 2004
INVENTOR(S) : Neidlein et al.

It is certified that error appears in the above-identified patent and that said Letters Patent is hereby corrected as shown below:

Title page,
Item [30], change from:
"[30]         Foreign Application Priority Data
August 6, 1998     (DE) .......................................... 199 36 514
December 4, 1999  (DE) .......................................... 198 55 850" to
-- [30]        Foreign Application Priority Data
August 6, 1998     (DE) .......................................... 199 36 514
December 4, 1998  (DE) .......................................... 198 55 850 --

Signed and Sealed this

Twenty-eighth Day of June, 2005

JON W. DUDAS
*Director of the United States Patent and Trademark Office*